(12) United States Patent
Dunfee

(10) Patent No.: US 7,186,378 B2
(45) Date of Patent: Mar. 6, 2007

(54) LIQUID SAMPLING PROBE AND CLEANING FLUIDICS SYSTEM

(75) Inventor: William David Dunfee, Newark, DE (US)

(73) Assignee: Dade Behring Inc., Deerfield, IL (US)

(\*) Notice: Subject to any disclaimer, the term of this patent is extended or adjusted under 35 U.S.C. 154(b) by 91 days.

(21) Appl. No.: 10/623,354

(22) Filed: Jul. 18, 2003

(65) Prior Publication Data

US 2005/0074363 A1    Apr. 7, 2005

(51) Int. Cl.
*B32B 5/02* (2006.01)

(52) U.S. Cl. ............... 422/63; 422/64; 422/65; 422/67; 422/99; 422/100; 436/180

(58) Field of Classification Search .......... 422/99–101, 422/104, 63–65; 436/180
See application file for complete search history.

(56) References Cited

U.S. PATENT DOCUMENTS

| | | | |
|---|---|---|---|
| 3,552,212 A | 1/1971 | Öhlin | |
| 3,964,526 A | 6/1976 | Sindermann et al. | |
| 4,318,885 A | 3/1982 | Suzuki et al. | |
| 4,323,537 A | 4/1982 | Mody | |
| 4,794,085 A | 12/1988 | Jessop et al. | |
| 4,926,701 A | 5/1990 | Tompkins | |
| 4,951,512 A | 8/1990 | Mazza et al. | |
| 4,951,513 A * | 8/1990 | Koike | 73/864.25 |
| 5,163,582 A | 11/1992 | Godolphin et al. | |
| 5,297,794 A | 3/1994 | Lu | |
| 5,347,878 A * | 9/1994 | Suovaniemi | 73/864.18 |
| 5,408,891 A | 4/1995 | Barber et al. | |
| 5,413,067 A | 5/1995 | Zarka et al. | |
| 5,413,246 A | 5/1995 | Godolphin et al. | |
| 5,499,545 A | 3/1996 | Kimura et al. | |
| 5,517,867 A | 5/1996 | Ely et al. | |
| 5,525,298 A | 6/1996 | Anami | |
| 5,531,960 A * | 7/1996 | Zelinka | 422/79 |
| 5,653,686 A | 8/1997 | Coulter et al. | |
| 5,827,744 A | 10/1998 | Fose et al. | |
| 5,918,291 A | 6/1999 | Inacu et al. | |
| 6,077,713 A | 6/2000 | Dunfee et al. | |
| 6,094,966 A | 8/2000 | Papen et al. | |
| 6,446,516 B1 | 9/2002 | Sullivan | |
| 6,627,156 B1 | 9/2003 | Goodale et al. | |

\* cited by examiner

*Primary Examiner*—Jill Warden
*Assistant Examiner*—Jyoti Nagpaul
(74) *Attorney, Agent, or Firm*—Leland K. Jordan

(57) ABSTRACT

A sampling aliquotter for aspirating aliquot portions of sample fluid from a closed container and for dispensing aliquot portions into a vessel using horizontal and vertical drives to drive a probe into the closed container, to position the probe above the vessel, and to lower the probe into a cleansing module.

5 Claims, 23 Drawing Sheets

LIQUID SAMPLING PROBE AND CLEANING FLUIDICS SYSTEM

FIELD OF THE INVENTION

The present invention relates to an automated apparatus for extracting liquid samples, particularly biological fluids such as urine, blood serum, plasma, cerebrospinal fluid and the like, from a container. In particular, the present invention provides a method to automatically extract a desired amount of sample fluid from a closed container in preparation for clinical diagnosis. The present invention is further related to a method and apparatus for cleaning liquid aspiration probes.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction cuvettes or tubes, incubated, and analyzed to aid in treatment of the patient. In typical clinical chemical analyses, one or two assay reagents are added at separate times to a liquid sample, the sample-reagent combination is mixed and incubated within a reaction cuvette. Analytical measurements using a beam of interrogating radiation interacting with the sample-reagent combination, for example turbidimetric absorption readings or the like, are made to ascertain end-point or reaction rate values from which the amount of an analyte may be determined using well-known calibration techniques.

Automated clinical analyzers are routinely required to remove all or a portion of sample fluid from collection containers and a number of sampling systems have been produced to assist this operation. Generally, these systems receive sample fluid containers, aspirate or remove a predetermined quantity of sample fluid from each container at a first location, and transfer the aspirated sample fluid to a second location for analysis. The sample fluid containers used with these systems are open-top vials or tubes transported in the system on carousels, racks or linear transports and then transferred between such devices with robotic mechanisms.

Using open sample fluid containers in a clinical laboratory presents a number of problems. First, the various devices which move the containers through the sampling system cause spills and contamination. Second, open sample fluid containers expose an operator to any harmful substances disposed in the containers. Finally, because open containers require special care, the cost of operation increases.

To avoid these problems, sample fluids to be tested in automated clinical analysis systems are often collected in evacuated glass tubes closed with caps like rubber stoppers and sealed with a vacuum. The sample fluid displaces part of the vacuum; but some vacuum may remain. Removal of the closure may result in the formation of aerosol particles. Consequently, when an operator removes the closure before placing the container in the automated system, the aerosol spray may expose the operator to any harmful substances contained in the sample fluid. In addition, removal of the closure manually by the operator increases the cost of operation and decreases the efficiency and reliability of an automated system.

A popular solution to these problems is to present a closed container containing the sample fluid to be analyzed to the automated analysis system and to employ an automated sampling system adapted to aspirate a known amount of sample fluid through the closure of a closed tube or vial. To do so, available sampling system include an arrangement of needles, purge mechanisms, gas pressurization and other complex techniques to take sample fluids from sealed sample fluid containers. In addition to requirements placed on these sampling systems to remove at least a predetermined amount of liquid, concerns remain over the quality of the extracted sample fluid, so that it be free of disruptive non-homogenities like clots or bubbles.

U.S. Pat. No. 4,794,085 describes an apparatus and a method which permit the detection of penetration of liquid by an apertured container used for aspirating and dispensing the liquid. The apparatus has control means for advancing the container an increment of the maximum possible distance to the liquid, means to generate a pressure differential within the dispensing container that is sufficient to generate a signal that is indicative of whether the container aperture is closed by the liquid, and devices to detect and signal the pressure produced within the container by such a pressure differential, and to compare the signaled pressure against a reference.

U.S. Pat. No. 4,926,701 describes a pipetting device comprising a probe for dipping into a reservoir, reaction vessel or the like, a metering pump connected to the probe and a shutoff valve disposed between the probe and the pump are provided. In the intake phase of the pump with the valve open, first air and then a predetermined quantity of liquid is taken in. For at least some of the delivery phase of the pump the valve is in the closed state so that a pressure builds up in the pump. At the end of the delivery phase the valve opens whereby due to the high pressure any adhering liquid particles are expelled.

U.S. Pat. No. 4,951,512 provides for providing access to a sealed container which temporarily provides an opening in the closures of the containers, and either removes contents, senses properties of the contents, or dispenses material into the container. A lift assembly moves each sample fluid container upward against a puncture tube to produce an opening in the closure of the container. The system takes a sample fluid through this opening or inserts a probe through the opening to measure the properties of the sample fluid.

U.S. Pat. No. 5,163,582 covers an apparatus and method for dispensing a predetermined volume of liquid from a closed, liquid-containing blood collection tube is described. The apparatus includes a dual conduit providing a passageway for liquid to be dispensed from a closed blood collection tube and a gas conduit providing a passageway for gas to be introduced into the blood collection tube. Included in the apparatus is insertion of the dual conduit into the blood collection tube, turning the tube away from a vertical, upright orientation, connecting and disconnecting the gas passageway from a gas supply, displacing a volume of gas through the gas passageway, and controlling the operation of the apparatus. A method is also disclosed involving insertion of a dual conduit into a closed blood collection tube, connecting a gas supply to a gas conduit of the dual conduit, rotating the tube away from a vertical, upright orientation, introducing a volume of gas corresponding to a signal into the blood collection tube, receiving a predetermined volume of liquid from the blood collection tube, and physically disconnecting the gas supply from the gas passageway.

U.S. Pat. No. 5,413,246 discloses a disposable apparatus to dispense an amount of liquid from a closed container using a closure piercing means to access the interior of a closed blood collection tube, a gas passage means to allow a metered amount of gas to be forced into the blood collection tube, and a liquid passage means to allow fluid to be dispensed from the tube in proportion to the amount of gas forced into the tube. Also disclosed is a machine which uses a disposable apparatus to dispense liquid from a sequence of closed blood collection tubes in an automated manner. Liquid contained within a blood collection tube is dispensed from the tube by a control means according to signals indicative of the amount of liquid within the tube and the amount of liquid that is desired to be dispensed. A manually operated machine that uses the disposable apparatus to dispense a sample of liquid from a closed blood collection tube is also described.

U.S. Pat. No. 5,499,545 is a method for improving measurement accuracy by eliminating the influence of changes in the atmospheric and internal pressures on the quantity of a liquid absorbed or discharged. A pipetting device inducts a specified quantity of liquid into a tip portion or discharges a specified quantity of liquid from the tip portion by controlling the pressure inside a cylinder portion including a cylinder and a piston. A control target value for the quantity of the liquid to be absorbed or discharged from a command portion and information from an atmospheric pressure measurement portion and a pressure sensor for detecting the internal pressure of the cylinder are sent to a correction calculation portion which in turn performs correction calculation based on measured data on the atmospheric and internal pressures and data on the shapes of the cylinder and tip portion to obtain the distance to be traveled by the piston so that the control target value form the command portion is met. A control portion controls a motor which drives the piston in accordance with information on the distance to be traveled by the piston from the correction calculation portion.

U.S. Pat. No. 5,517,867 discloses an apparatus for extracting a liquid from either an open or a closed liquid container. An upper arm carries a depending single extraction needle at a first lateral end in alignment with a closure penetration axis. A foot attached to a lower arm has a conically shaped surface therein and a central axial bore aligned vertically with the penetration axis. The upper and the lower arms move as a unit until the conically shaped surface on the foot abuts the upper end of a container. This abutting action between the conical surface on the lower arm and the container draws the container into and secures the container in an operating position in which the axis of the container is collinear with the penetration axis. Continued displacement of the upper arm by the actuator with respect to the lower arm extends the extraction needle from the bore and causes the needle to penetrate through the closure. A pair of vertically extending plates is attached to the lower arm. The combination of the plates and the lower arm has sufficient weight to generate a holding force that retains the container in the operating position when an acutator displaces the upper arm to withdraw the extraction needle through the closure and from the container.

U.S. Pat. No. 5,525,298 discloses a device for delivering a serum sample from a blood collection tube into one or more sample vessels or reaction vessels, including a pair of arms which are arranged movably in opposite directions, a motor for driving the arms to selectively grasp the blood collection tube, a block to which the arms are provided, a motor for rotating the block over 135 degrees, a needle-like suction nozzle secured to the block, a syringe having a main body coupled with the suction nozzle and a piston arranged movably within the main body, a motor for driving a piston of the syringe, a slide block on which the block is arranged rotatably, a motor for moving the slide block in right and left directions, a base member arranged movably up and down, and a motor for driving the base member up and down. After the blood collection tube is picked out of a rack by the arms, the base member is moved downward to insert the suction nozzle into the container through the cap, and then the block is rotated to turn over the blood collection tube. Then, the serum sample is sucked by operating the syringe, and then the block is rotated into an initial position. After the suction nozzle is pulled out of the cap, a given amount of the sucked serum sample is discharged into one or more sample vessels or reaction vessels.

U.S. Pat. No. 5,413,067 discloses a sampler mechanism for fluidly interconnecting a ball valve with the interior space of a septum closed container for the taking of closed loop samples of fluid materials. The sampler mechanism includes a needle assembly having a hollow needle and a needle seating collar which is positioned adjacent the ball in the ball valve, a threaded injector end fitting for attaching and securing the needle assembly to the ball valve, and an injector body for fluidly connecting the ball valve to the container and for providing a fluid passageway for fluid communication between the container and a side surface of the injector body.

A common problem in liquid aspirating systems like those described above is the risk of liquid "adhesion" and/or "carryover". Carryover occurs when a probe having residual traces of a previously dispensed sample or reagent is introduced into volume of a different reagent or sample. Carryover is usually manifested as the contamination of a given reagent supply or a given-sample volume by the introduction thereinto of other reagents or samples that remain on or in or are adsorbed by the sample probe. Adhesion occurs when a portion of an aspirated reagent or sample adheres to the exterior surface of a sample probe and is not appropriately removed therefrom.

To minimize adhesion and/or carryover, the sample fluid probe is generally cleaned by washing prior to subsequent operations. Washing is typically accomplished by lowering the sample fluid probe into a cleaning resource that contains an appropriate cleaning liquid solution. The cleaning liquid solution washes the exterior of the sample fluid probe. The interior of the sample fluid probe is cleaned by aspirating and discharging the cleaning solution. Alternatively, the sample fluid probe may be cleaned by discharging a purge liquid through the sample fluid probe into a drain. Washing may use a jet of drying air forced under pressure through the sample fluid probe or at the exterior surface thereof. In this manner the volume of residual carryover on the exterior surface or the interior of the sample fluid probe is minimized. As a practical matter, cleaning of both the sample fluid probe and cleaning resource is required to preserve proper operation.

Analysis instruments having a typical sample fluid probe wash station are described in U.S. Pat. No. 3,964,526 (Sindermann), U.S. Pat. No. 4,318,885 (Suzuki et al.) and U.S. Pat. No. 3,552,212 (Ohlin), and U.S. Pat. No. 4,323,537 (Mody). A common problem with sample fluid probe washing, however, is residual liquid or contaminants may be adsorbed on the sample fluid probe despite washing. This residue may mix with subsequent sample fluids or reagents drawn into the sample fluid probe and can result in the introduction of a contaminated sample fluid or reagent. Furthermore, the presence of additional residual droplets of sample fluid or reagent on the exterior or interior of the sample fluid probe may cause unwanted additional liquid to be introduced into a destination receptacle. This unwanted residue may mix with subsequent sample fluid or reagents drawn into the sample fluid probe and interfere with chemical analyses. Sample fluid probe cleaning is a particularly troublesome problem when exacerbated by the trend to smaller and smaller sample fluid volumes. A minute volume of cleaning liquid solution may remain within or on the exterior surface of a sample fluid probe causing a corresponding deficiency in the volume of sample fluid later transferred to a reaction vessel. Such a sample fluid volume deficiency may create serious analytical errors in automated assays for calcium, magnesium and glucose, in particular.

U.S. Pat. No. 8,827,744 discloses a method for cleaning a liquid sample probe in which the probe is positioned within a washing chamber inside a wash body and a purging liquid solution is pumped through the probe into the chamber. A cleaning liquid solution may also be pumped into the chamber around the probe. Either or both liquids are subsequently vacuumed from the chamber drawing air through an annular gap between the probe and the wash body thereby creating a cleaning air flow between the exterior probe surface and the wash body. The cleaning air flow removes all cleaning liquid solution and/or purging liquid solution as the probe is removed from the wash body.

U.S. Pat. No. 5,297,794 addresses this problem by using flushing water in combination with an inclined waterway channel in which the sample probe is immersed. As the sample probe traverses the waterway channel, it is withdrawn and liquid communication between the waterway and the sample probe is broken and cleaning ceases, leaving liquid droplets on the sample probe.

U.S. Pat. No. 5,408,891 also addresses this problem and used a wash collar with (1) pressurized water supplied through the inner bore of a fluid sample probe to wash the inside of the sample probe, and (2) a separate supply of water washing the sample probe and the exterior of the sample probe when positioned in a small central chamber within the wash collar. The wash collar is of complex design including five differently shaped portions through a central bore in which the sample probe moves. The water is drawn away from the sample probe and out of the wash collar through a vacuum port located in the lower portion of the bore and in communication with a vacuum source. Unfortunately, only a small portion of external air enters the wash collar from the direction of sample probe insertion, the majority coming from an enlarged lowermost portion of the wash collar bore. This does not permit thorough cleaning of the sample probe.

Accordingly, from a study of the different approaches taken in the prior art to the problems presented by the necessity for aspirating a liquid from a closed liquid container with a sample fluid probe, coupled with the necessity for effectively cleaning the sample fluid probe between sample fluid aspirations within an automated clinical analyzer, it is believed advantageous to provide a cleaning method which effectively eliminates extraneous material from the full interior and the full exterior of a sample fluid probe while at the same time not unduly adding to the complexity of washing resources. It is believed to be highly advantageous for such a sampling system to be adapted to aspirate liquid from a closed liquid container without complex control mechanisms or unduly adding to the aspiration resources required.

SUMMARY OF THE INVENTION

Many of these prior art deficiencies are reduced with the present invention which relates to a method for aspiration from a closed sample fluid tube with a sample fluid probe, the sample fluid probe having an interior hollow portion and an exterior surface, the hollow portion in communication with resources of a interior probe cleansing system. The sample fluid probe is supported by a manifold and is moveable into and out of a bore within a washing body in communication with an exterior probe cleansing system.

Cleaning the probe comprises positioning the sample fluid probe within the bore and pumping cleansing and rinsing solutions into the hollow portion, followed by pressurized drying air. Subsequently, the exterior portion of the probe is subjected to a flow of cleansing and rinsing solutions, followed by pressurized drying air.

Aspiration of liquid from closed sample fluid tubes comprises positioning the sample fluid probe over a closure, lowering the sample fluid probe through an opening in a sample tube retainer so that the probe penetrates the closure and reaches a predetermined distance below the sample fluid level. A locking mechanism alternately locks the probe or the retainer in the vertical direction. After aspiration, The tube retainers are positioned against the closure and the manifold raised to remove the probe from the sample fluid tube. In this operation, the sample fluid probe is moved by the manifold also used to clean the probe within the washing body.

BRIEF DESCRIPTION OF THE DRAWINGS

The invention will be more fully understood from the following detailed description thereof taken in connection with the accompanying drawings which form a part of this application and in which.

DESCRIPTION OF THE PREFERRED EMBODIMENTS

Figure 1:
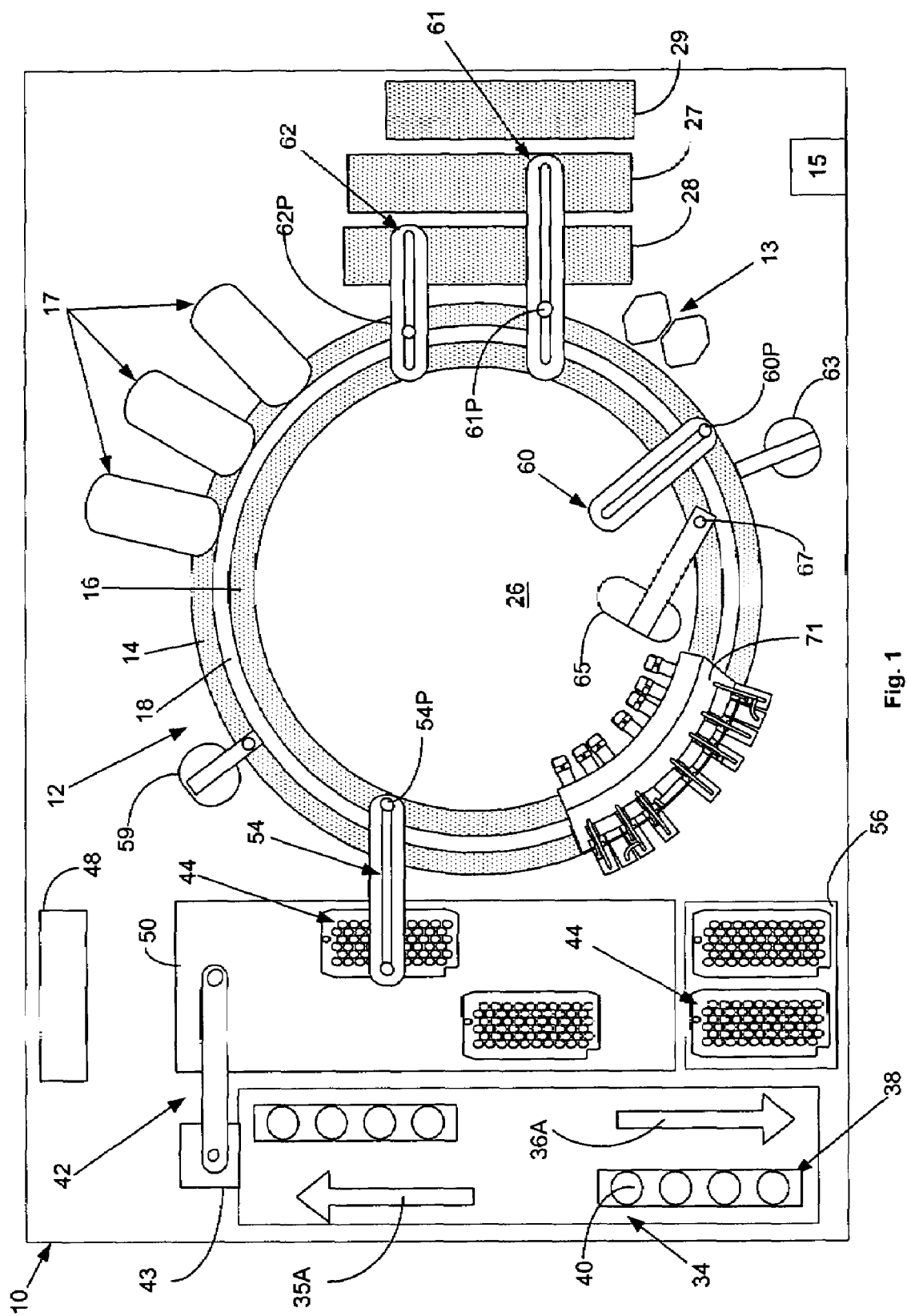
FIG. 1 is a schematic plan view of an automated analyzer in which the present invention may be employed to advantage.
Figure 2:
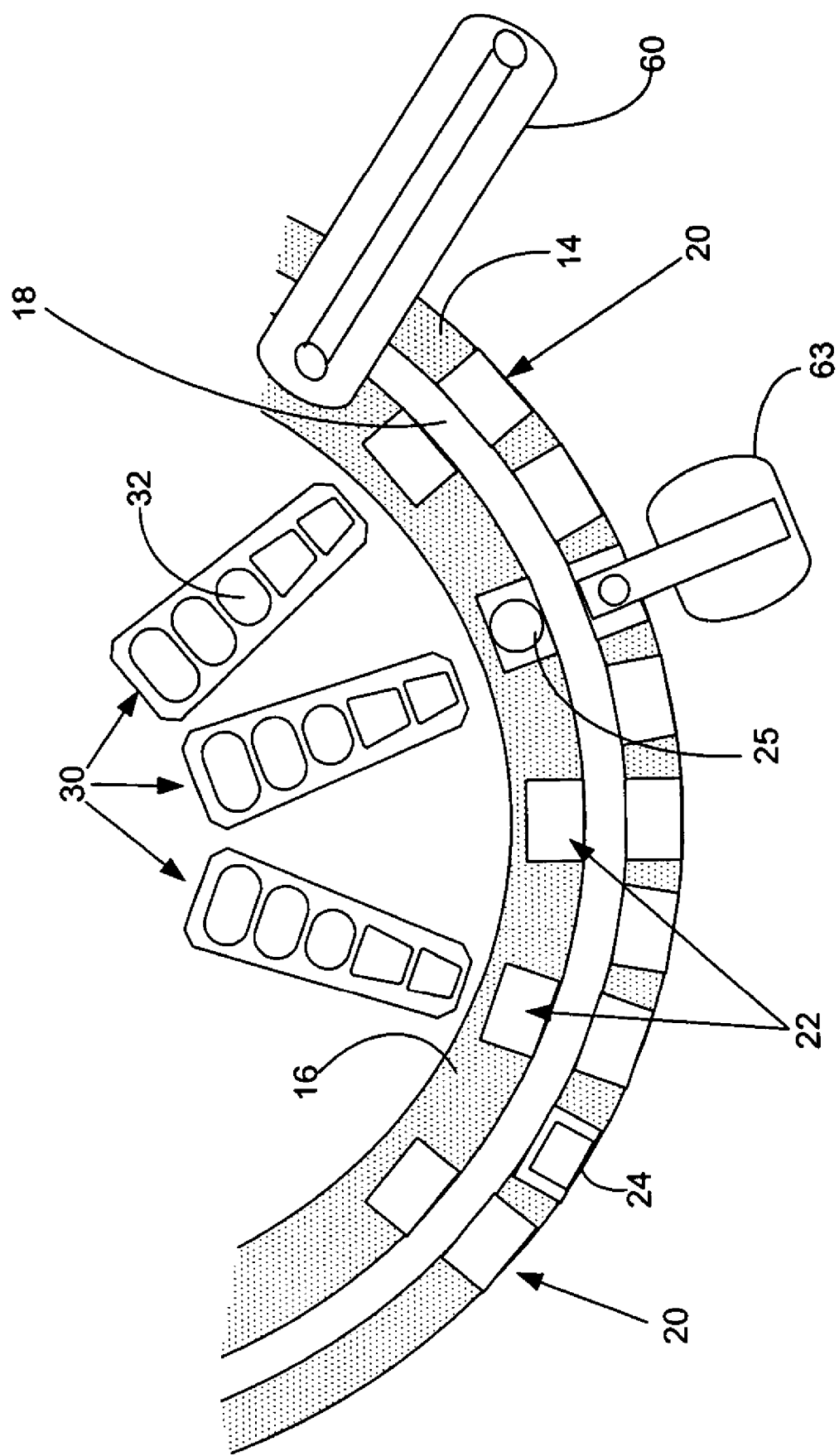
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18.

Cuvette ports 20 are adapted to receive a plurality of reaction cuvettes 24 that contain various reagents and sample fluids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within a cuvette 24.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10 as well as the operation of operational devices 13.

Figure 3:
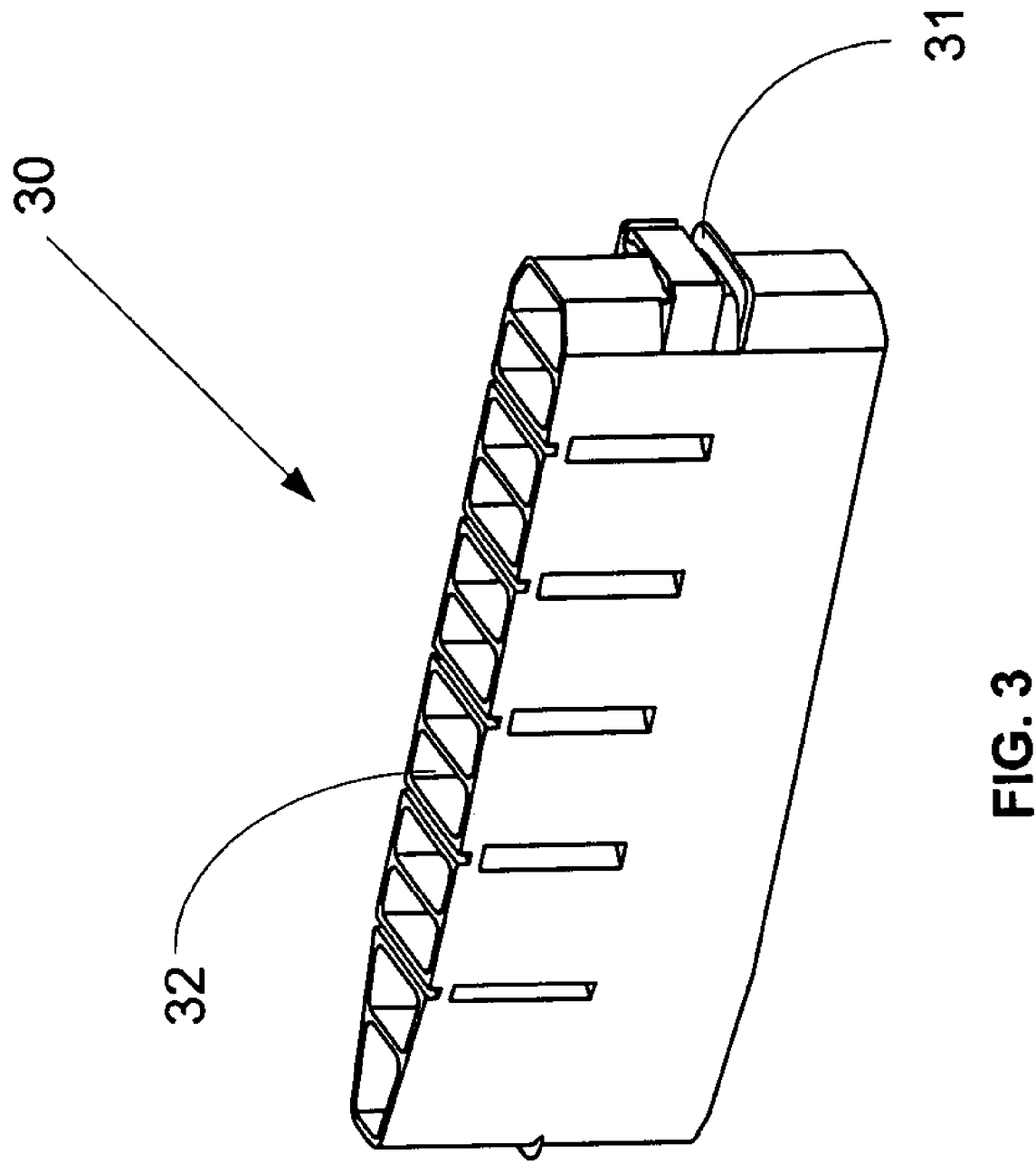
FIG. 3 is a perspective view of a reaction container useful in the analyzer of FIG. 1.

Temperature-controlled reagent storage areas 26, 27 and 28 store a plurality of multi-compartment elongate reagent cartridges 30 like that illustrated in FIG. 3 and described in patent publication number 2003-0049848 assigned to the assignee of the present invention, and containing reagents in wells 32 as necessary to perform a given assay. A lock-out device 31 is provided to prevent accidental re-use of a previously used reagent container 30. Reagent storage area 26 comprises at least one reagent operation carousel where operations like reagent preparation and reagent aspiration take place. Reagent containers 30 may be loaded by an operator by placing such containers 30 into a container loading tray 29 adapted to automatically translate containers 30 to a shuttling position as described in patent publication number 2005-0013735, assigned to the assignee of the present invention.

Figure 4:
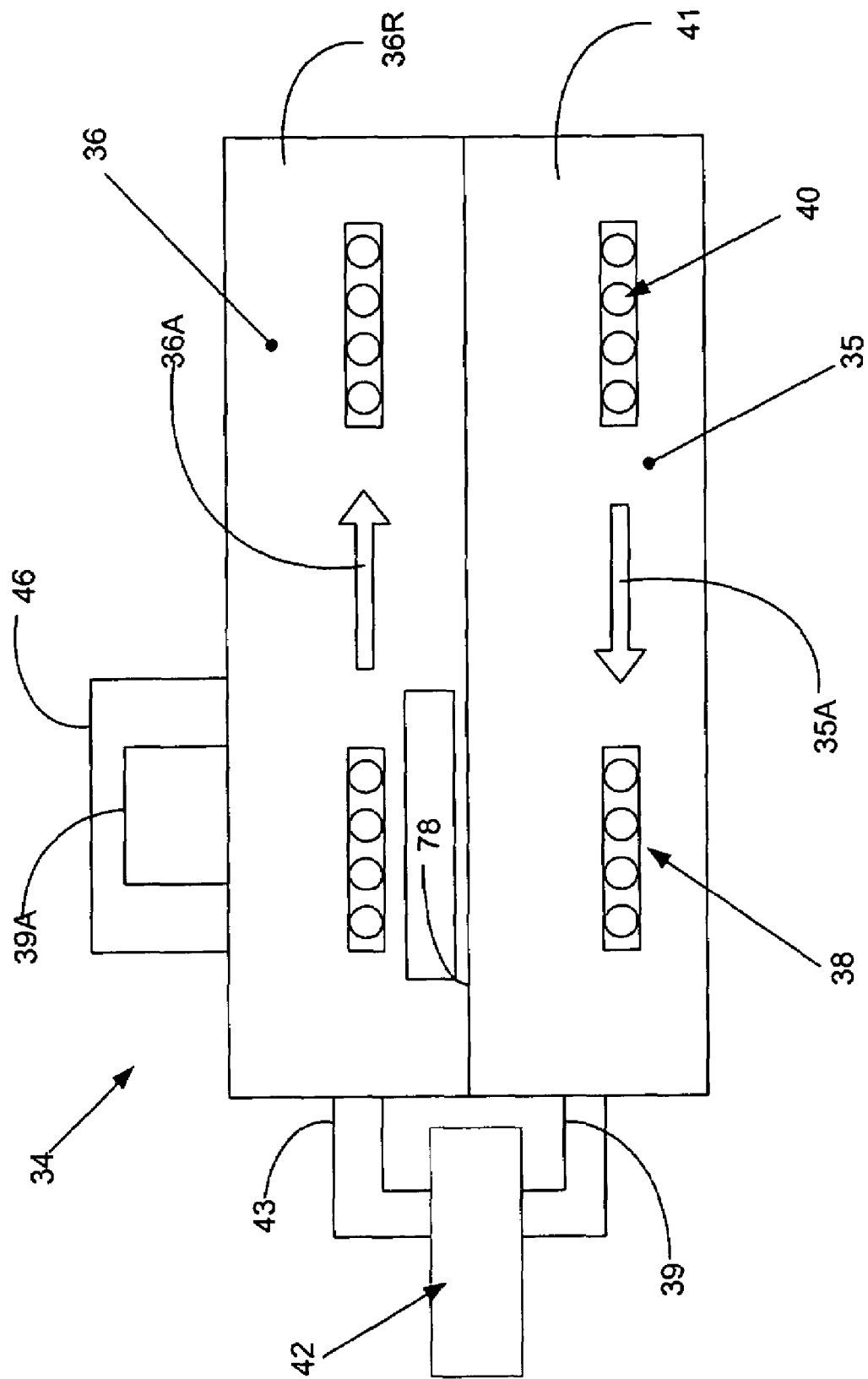
FIG. 4 is perspective elevation view of an aliquot vessel array useful in the analyzer of FIG. 1.
Figure 5:
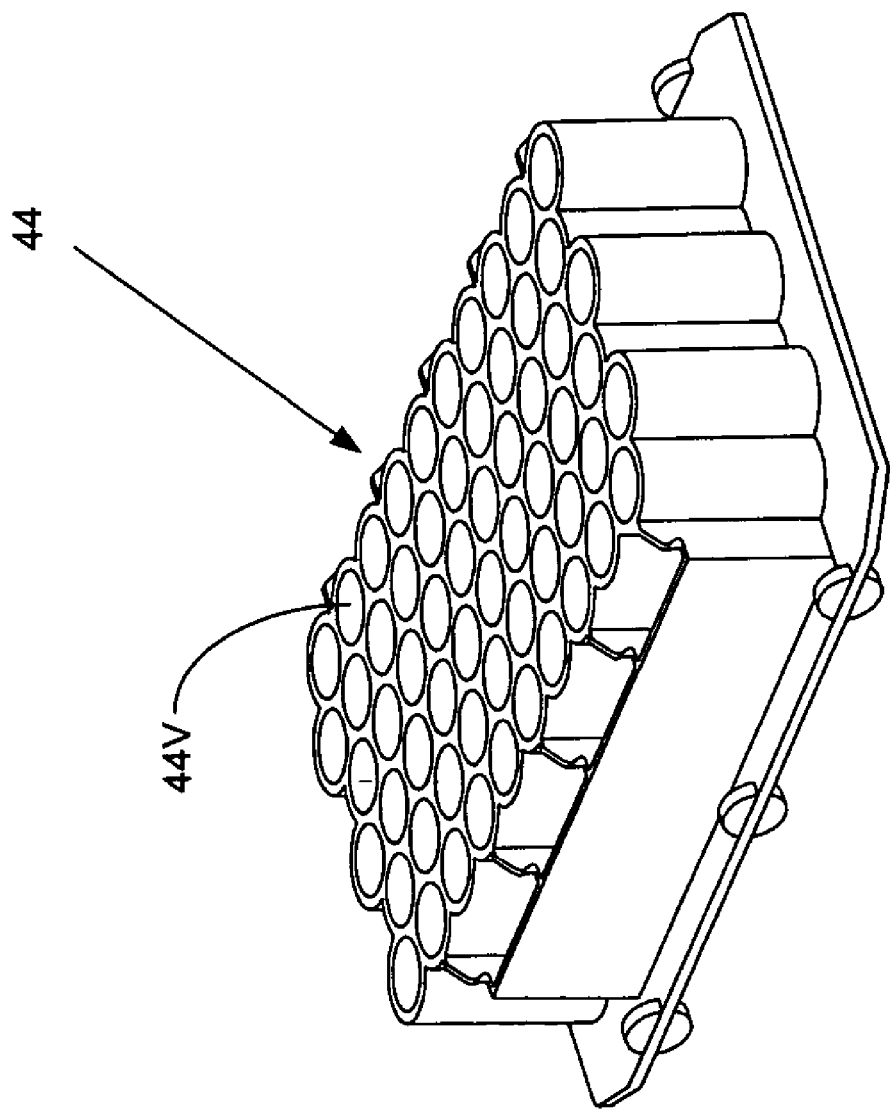
FIG. 5 is a perspective elevation view of an automated aliquot vessel array storage and handling unit of the analyzer of FIG. 1.

As seen in FIG. 4, a bi-directional incoming and outgoing sample fluid tube transport system 34 described in patent publication number 2003-0049848 assigned to the assignee of the present invention, comprises an input lane 35 and an output lane 36 formed along a top operating surface of analyzer 10. Input lane 35, taken with a magnetic drive system described in said co-pending application, transports sample fluid tube racks 38 containing open or closed sample fluid containers such as sample fluid tubes 40 from a rack input load position 41 at a first end of the input lane 35 right-to-left along the length of input lane 35 as indicated by open arrow 35A. A liquid sampling aliquotter 42, exemplifying the present invention and described hereinafter, is located proximate a second end of the input lane 35 opposite the first end of lane 35. Once a rack 38 containing sample fluid tubes 40 is proximate aliquotter 42, rack 38 may be retained in a liquid sampling zone 43 by a shuttle mechanism 39 while aliquotter 42 is operable to aspirate aliquot portions of sample fluid from sample fluid tubes 40 and to dispense an aliquot portion of the sample fluid into one or more of a plurality of vessels 44V in aliquot vessel array 44, seen in FIG. 5 and described in patent publication number 2003-0129095 assigned to the assignee of the present invention, depending on the quantity of sample fluid required to perform the requisite assays and to provide for a sample fluid aliquot to be retained by analyzer 10 within environmental chamber 48 described in patent publication number 2002-0064881 assigned to the assignee of the present invention.

After a volume of sample fluid is aspirated from all sample fluid tubes 40 on a rack 38 and dispensed into aliquot vessels 44V by sampling aliquotter 42 of the present invention described later, a rack 38 may be held in a buffer zone 46 until a successful assay result is obtained. Regardless of whether sample fluid racks 38 are held in the sampling zone 43 or buffer zone 46, shuttle mechanism 39 or a shuttle mechanism 39A associated with buffer zone 46 positions the sample fluid rack 38 onto output lane 36. Output lane 36, taken with the magnetic drive system, moves racks 38 containing sample fluid tubes 40 toward the rightmost end 36R of the input lane 36 as indicated by open arrow 36A to a frontal area of analyzer 10 which is readily accessible to an operator so that racks 38 may be conveniently unloaded from analyzer 10.

Liquid specimens contained in sample fluid tubes 40 are identified by reading bar coded indicia placed thereon using a conventional bar code reader to determine, among other items, a patient's identity, the tests to be performed, if a sample fluid aliquot is to be retained within analyzer 10 and if so, for what period of time. It is also common practice to place bar coded indicia on sample fluid tube racks 38 and employ a large number of bar code readers installed throughout analyzer 10 to ascertain, control and track the location of sample fluid tubes 40 and sample fluid tube racks 38.

Figure 6:
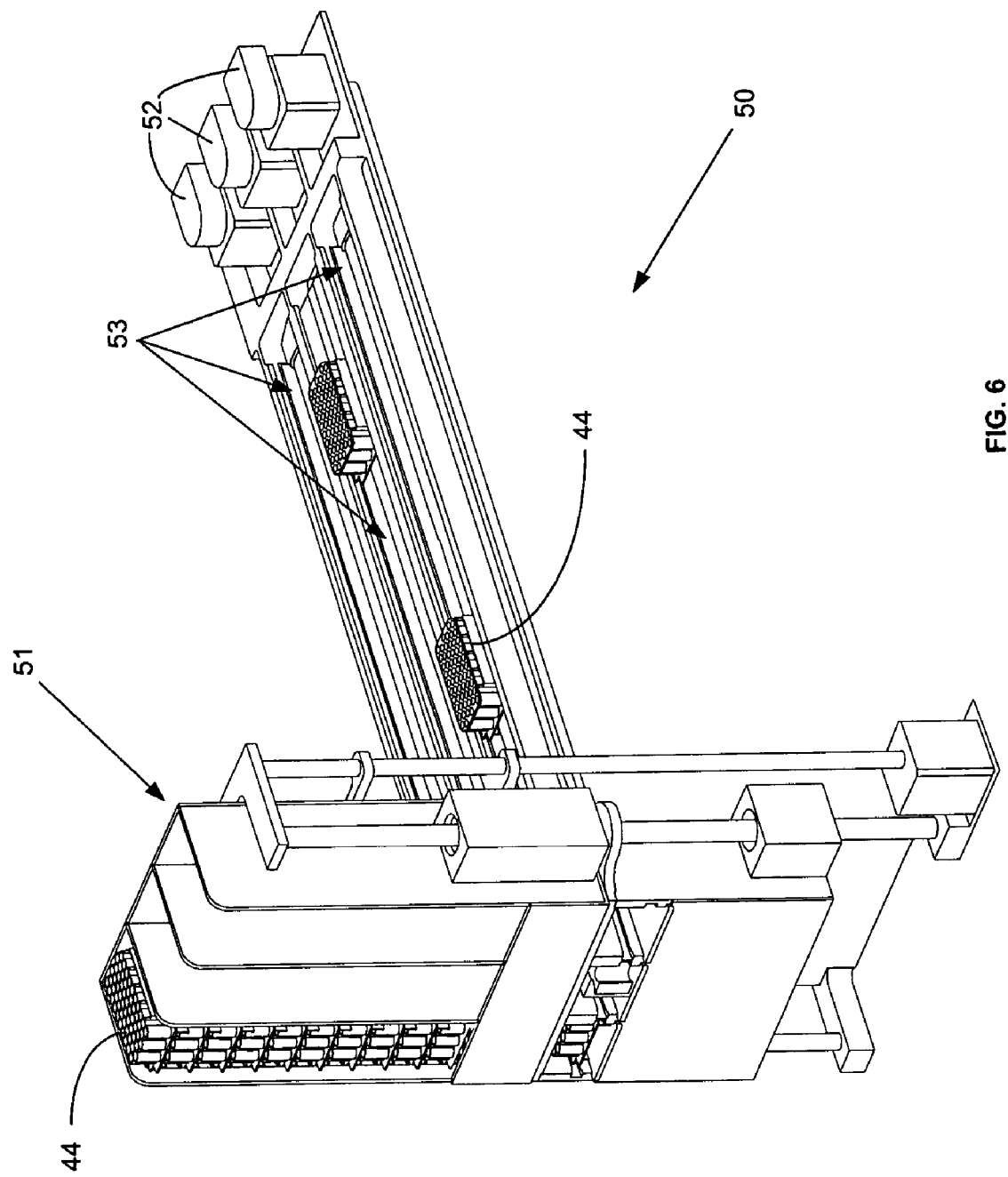
FIG. 6 is a perspective view of a transport system for transporting the aliquot vessel array of FIG. 4.

Aliquot vessel array transport system 50 seen in FIG. 6 comprises an aliquot vessel array storage and dispense module 51 and a number of linear drive motors 52 adapted to bi-directionally translate aliquot vessel arrays 44 within a number of aliquot vessel array tracks 53 below a sample fluid aspiration and dispense arm 54 located proximate reaction carousel 12, as seen in FIG. 1. Sample fluid aspiration and dispense arm 54 is controlled by computer 15 and is adapted to aspirate a controlled amount of sample fluid from individual vessels 44V positioned at a sampling location within a track 53 using a conventional liquid probe 54P and then liquid probe 54P is shuttled to a dispensing location where an appropriate amount of aspirated sample fluid is dispensed into one or more cuvettes 24 in cuvette ports 20 for testing by analyzer 10. After sample fluid has been dispensed into reaction cuvettes 24, conventional transfer means move aliquot vessel arrays 44 as required between aliquot vessel array transport system 50, environmental chamber 48 and a disposal area, not shown.

A number of reagent aspiration and dispense arms 60, 61 and 62 comprising conventional liquid reagent probes, 60P, 61P and 62P, respectively, are independently mounted and translatable between reagent storage areas 26, 27 and 28, respectively and outer cuvette carousel 14. Probes 60P, 61P and 62P comprise conventional mechanisms for aspirating reagents required to conduct specified assays at a reagenting location from wells 32 in an appropriate reagent cartridge 30, the probes 60P, 61P and 62P subsequently being shuttled to a reagent dispensing location where reagent(s) are dispensed into reaction cuvettes 24 in outer cuvette carousel 14. Additional probes may be provided to provide increased flexibility if desired. A number of reagent cartridges 30 are inventoried in controlled environmental conditions inside reagent storage areas 26, 27 and 28 and may be transported thereto as required from loading tray 29.

Reaction cuvette load station 63 and reaction vessel load station 65 are respectively positioned proximate outer cuvette carousel 14 and inner vessel carousel 16 and are adapted to load reaction cuvettes 24 into cuvette ports 20 and reaction vessels 25 into vessel ports 22 using for example a sliding chute 67. In operation, used cuvettes 24 in which an assay has been finally conducted, are washed and dried in a wash station 71 like disclosed in patent publication number 2005/0014274 assigned to the assignee of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 65 like that on load stations 63 and 65.

Figure 7:
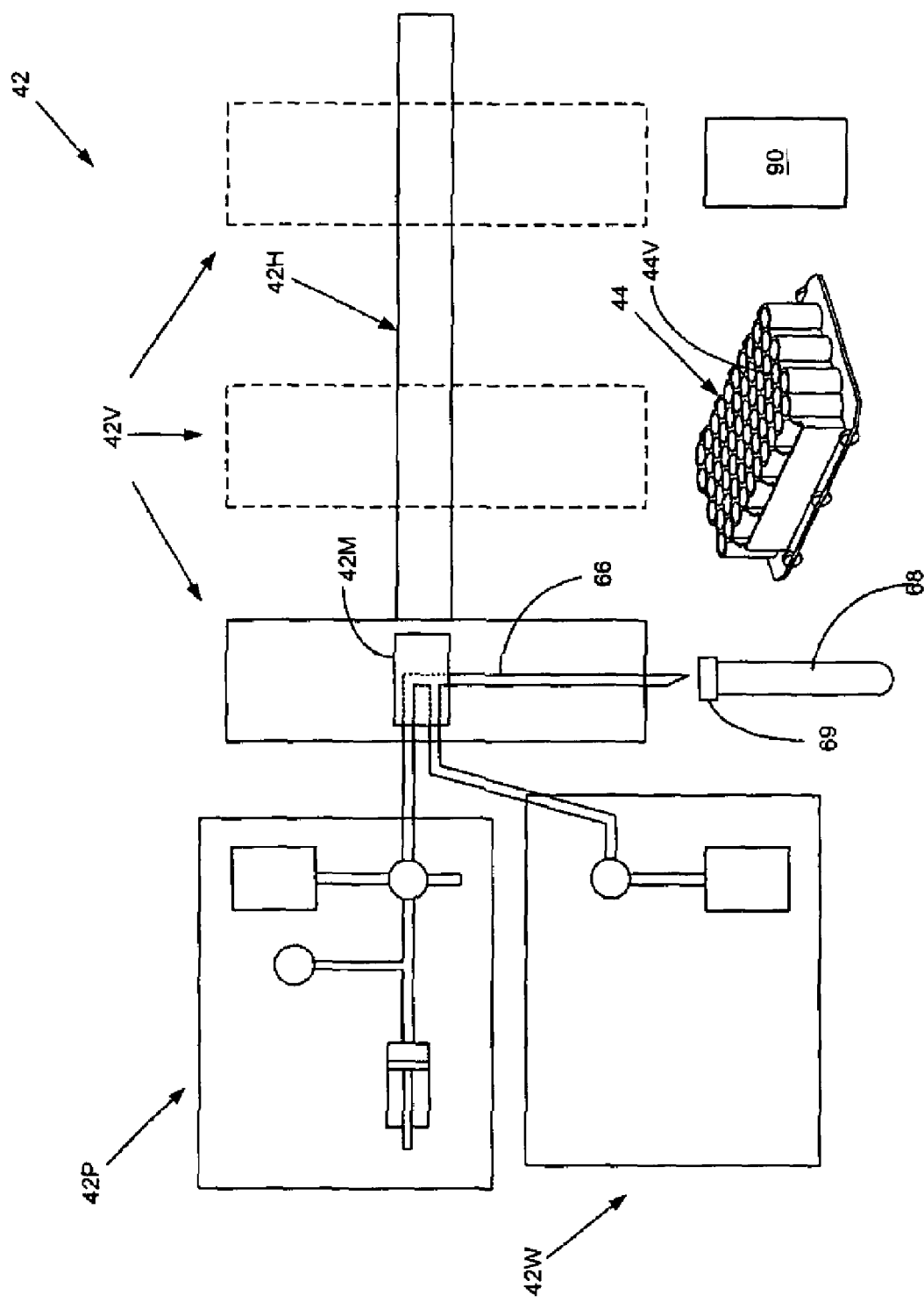
FIGS. 7, 8, 9, 9A, 10, 11A, 11B and 11C schematically describe a sample fluid aliquotting process using the sampling system of the present invention.

Sampling aliquotter 42 exemplifies the present invention and is seen in FIG. 7 to comprise a Horizontal Drive 42H, a Vertical Drive 42V, a Wash Module 42W, a Pump Module 42P and a Cleansing Module 90 having the primary functions described in Table 1. Components of the Wash Module 42W and Pump Module 42P unidentified in FIG. 7 will be described later.

TABLE 1

| Module | Primary Functions |
| --- | --- |
| Horizontal Drive 42H | 1. Position the Vertical Drive 42V over sample fluid tubes 40 on a rack 38, over individual vessels 44V of aliquot vessel arrays 44 and over Cleansing Module 90 |
| Vertical Drive 42V | 1. Position a probe 66 at vertical positions for aspiration and dispense operations |
|  | 2. Drive probe 66 through the closure 69 of a sample fluid container 40 |
|  | 3. Determine liquid level of sample fluid 68 |
|  | 4. Monitor aspiration quality |
| Wash Module 42W | 1. Remove contamination from probe 66 with liquid cleansing solutions |
| Cleansing Module 90 | 1. Cleansing interior and exterior surfaces of sample fluid probe 66 |
| Pump Module 42P | 1. Aspirate and dispense sample fluid |
|  | 2. Wash probe 66 |
| Wash Manifold 42M | 1. Connect Wash Module 42W and Pump Module 42P to probe 66 |

Figure 8:
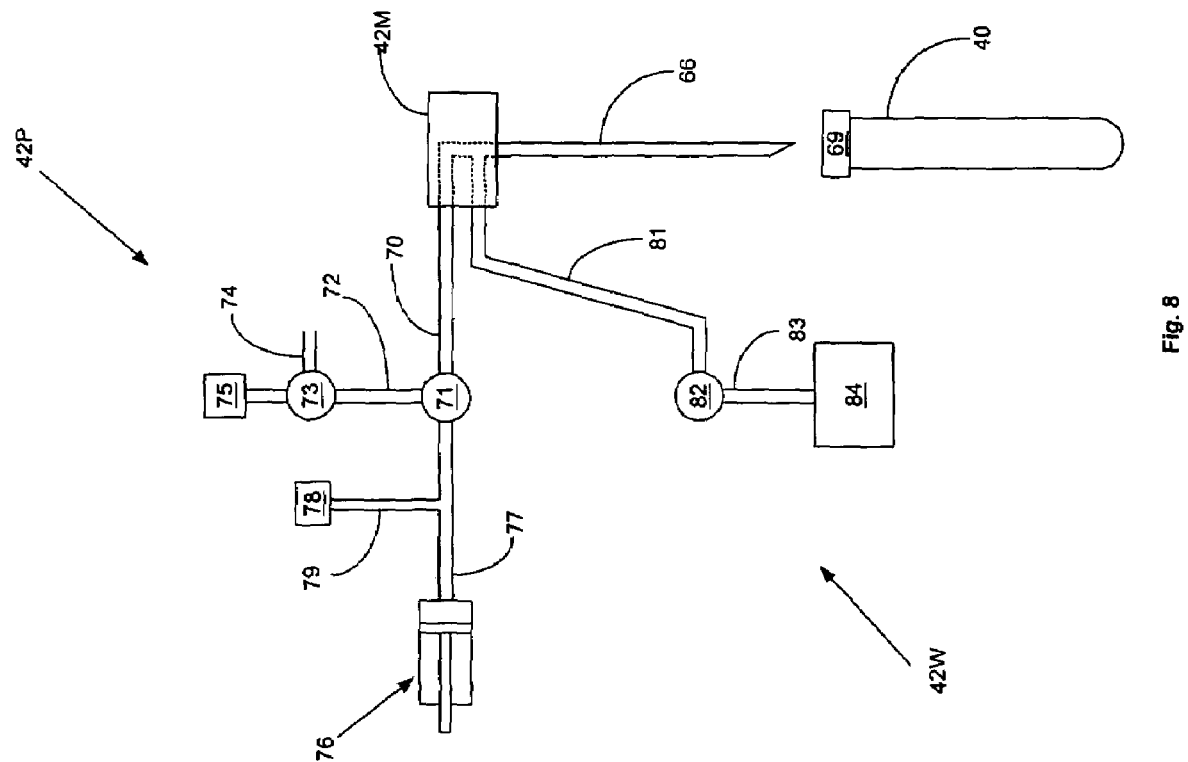

FIG. 8 shows Pump Module 42P connected to conventional hollow, liquid-carrying probe 66 having conventionally defined interior and exterior surfaces and supported by Wash Manifold 42M, the Wash Manifold 42M being connected by a hollow air tube 70 to a three-way valve 71. Probe 66 preferably has a tapered point designed to reduce coring effects when inserted through closure 69 and may be connected to Wash Manifold 42M using any of several screw-like connectors, not shown, or alternately, permanently welded thereto. Valve 71 is operable to optionally connect air tube 70 to (1) a vent valve 73 connected to an atmospheric vent tube 74 and an air supply 75, or to (2) a piston-type syringe pump 76 by a hollow air tube 77. A conventional air pressure measuring transducer 78 is connected to air tube 77 between pump 76 and valve 71 by a hollow air tube 79.

Figure 9:
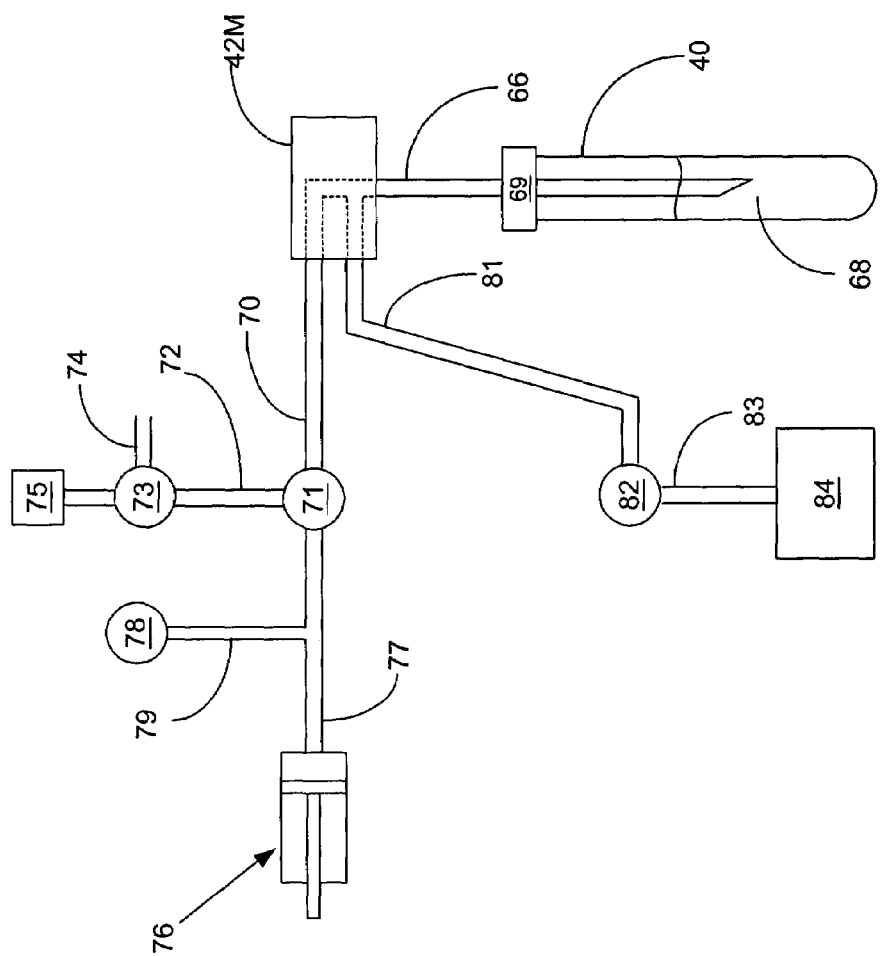
Figure 9A:
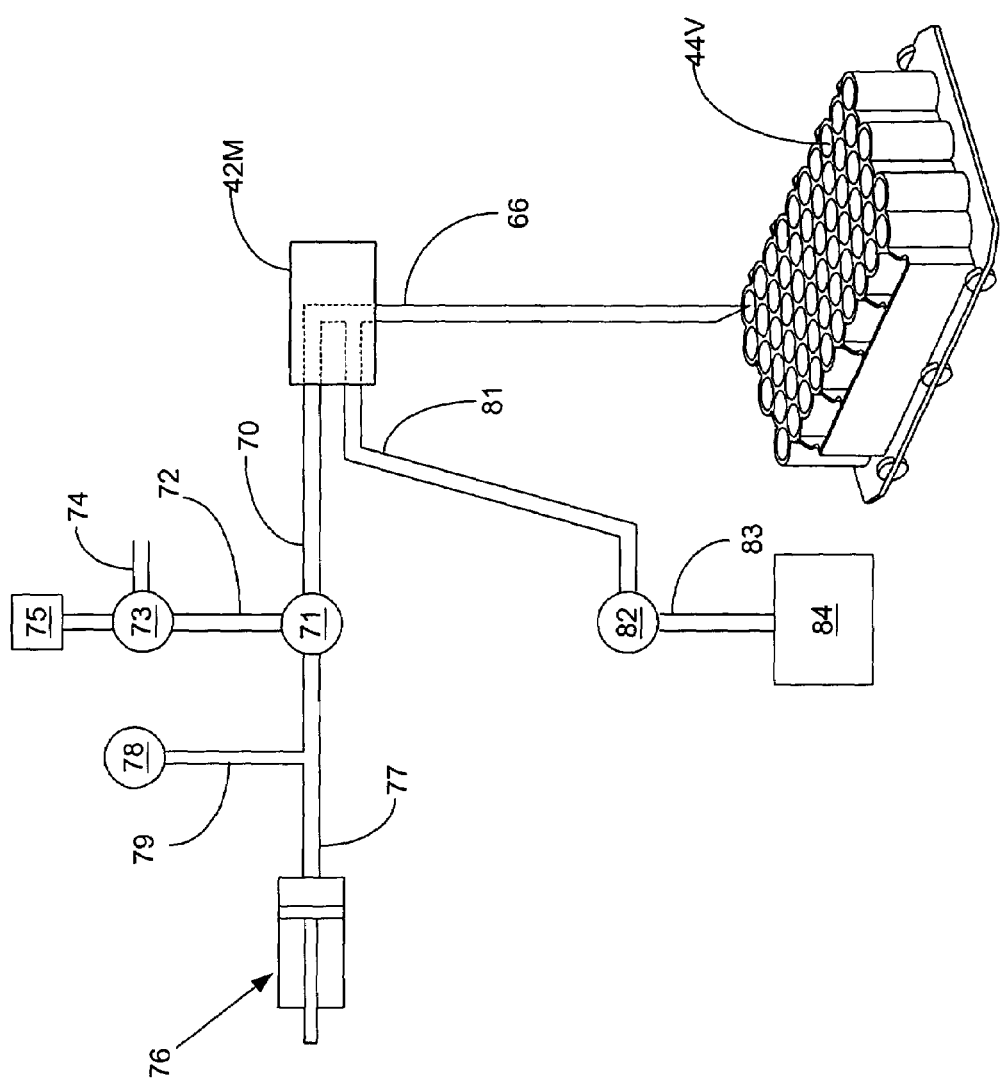

FIG. 9 illustrates sample fluid probe 66 having punctured closure 69, as explained in conjunction with FIGS. 8–9, and positioned within sample fluid 68 contained in sample fluid tube 40. Such a closure puncturing process is a key feature of the present invention and is described hereinafter in greater detail. Clearly if the sample tube 40 is not closed by a closure, puncturing is not required. Level sensing means, for example using well known capacitive signals, are may be advantageously employed in order to ensure that probe 66 is in fluid communication with sample fluid 68. Piston 76 is activated and the distance it is moved is controlled by computer 15 so that a controlled volume of sample fluid 68 is withdrawn or aspirated into probe 66. During this process, valve 71 is closed to vent tube 72, but is open to air tube 77 and air tube 70. After aspiration of sample fluid 68 from sample fluid tube 40 is completed, Wash Manifold 42M is raised by Vertical Drive 42V as explained hereinafter and positioned by Horizontal Drive 42H so that probe 66 may dispense sample fluid 68 into vessels 44V in aliquot vessel arrays 44, as seen in FIG. 9A. Vertical Drive 42V and Horizontal Drive 42H are similarly operated to effect the movements of probe 66 as described next in a cleansing operation thereof. FIG. 8 also shows Wash Manifold 42W as comprising a flush valve 82 connected to Wash Manifold 42M by a hollow liquid carrying tube 81. Flush valve 82 is operable to connect liquid carrying tube 81 to a pressurized rinse water source 84 by a hollow liquid tube 83.

Figure 10:
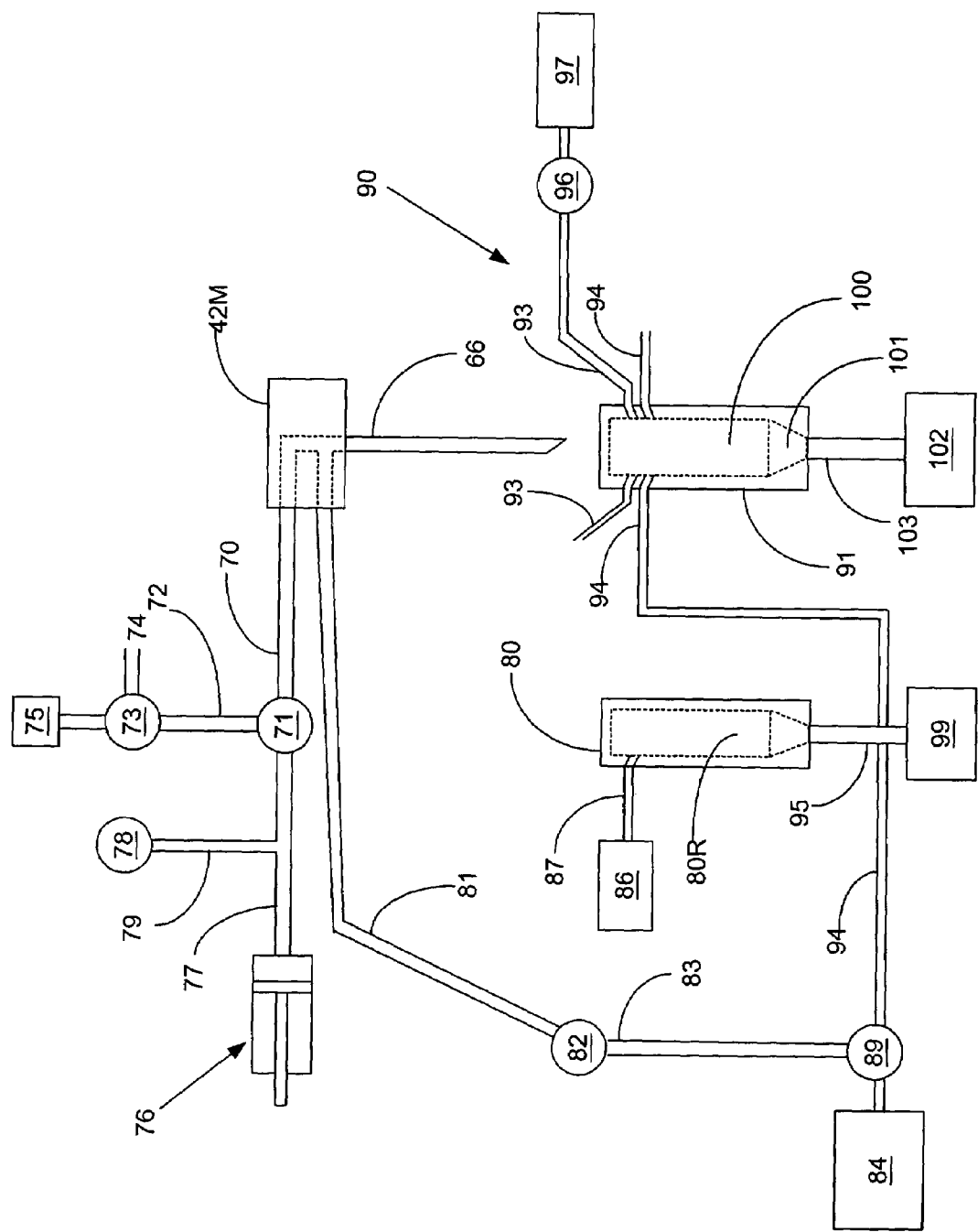

FIG. 10 shows a Cleansing Module 90 constructed in accordance with a preferred embodiment of the present invention and comprising a first open cleansing body 91 having two pairs of tubings 93 and 94 ported thereto on opposite sides of cleansing body 91 in the upper portion of first cleansing body 91. Uppermost ported tubing 93 is connected to an air knife valve 96 and therefrom to an air knife supply source 97; ported tubing 94 is connected to inlet valve 83 and therefrom to pressurized rinse water source 84. Tubings 93 and 94 may be ported or joined to the first cleansing body 91 using conventional threaded fittings; however, use of barbed port-tubing connections for vacuum lines has the advantage of making it unlikely that tubings will be inadvertently dislodged. Cleansing Module 90 further comprises a second open cleansing body 80 connected at its bottom to a bleach-like cleansing solution source 99 and at its top to a vacuum source 86. Cleansing solution source 99 is operated to maintain the internal reservoir 80R of second open cleansing body 80 filled with a bleach-like cleansing solution with the excess bleach-like cleansing solution drawn away by vacuum source 86.

FIG. 10 further shows cleansing body 91 as having a vertically oriented, generally circular, internal cleansing chamber 100 formed therein and having a tapered bottom portion 101, both shown in dotted lines, the cleansing chamber 100 being in vacuum communication with a vacuum style waste reservoir 102 by means of a vacuum tube 103. The internal reservoir 80R of second open cleansing body 80 is similarly shaped.

Figure 11A:
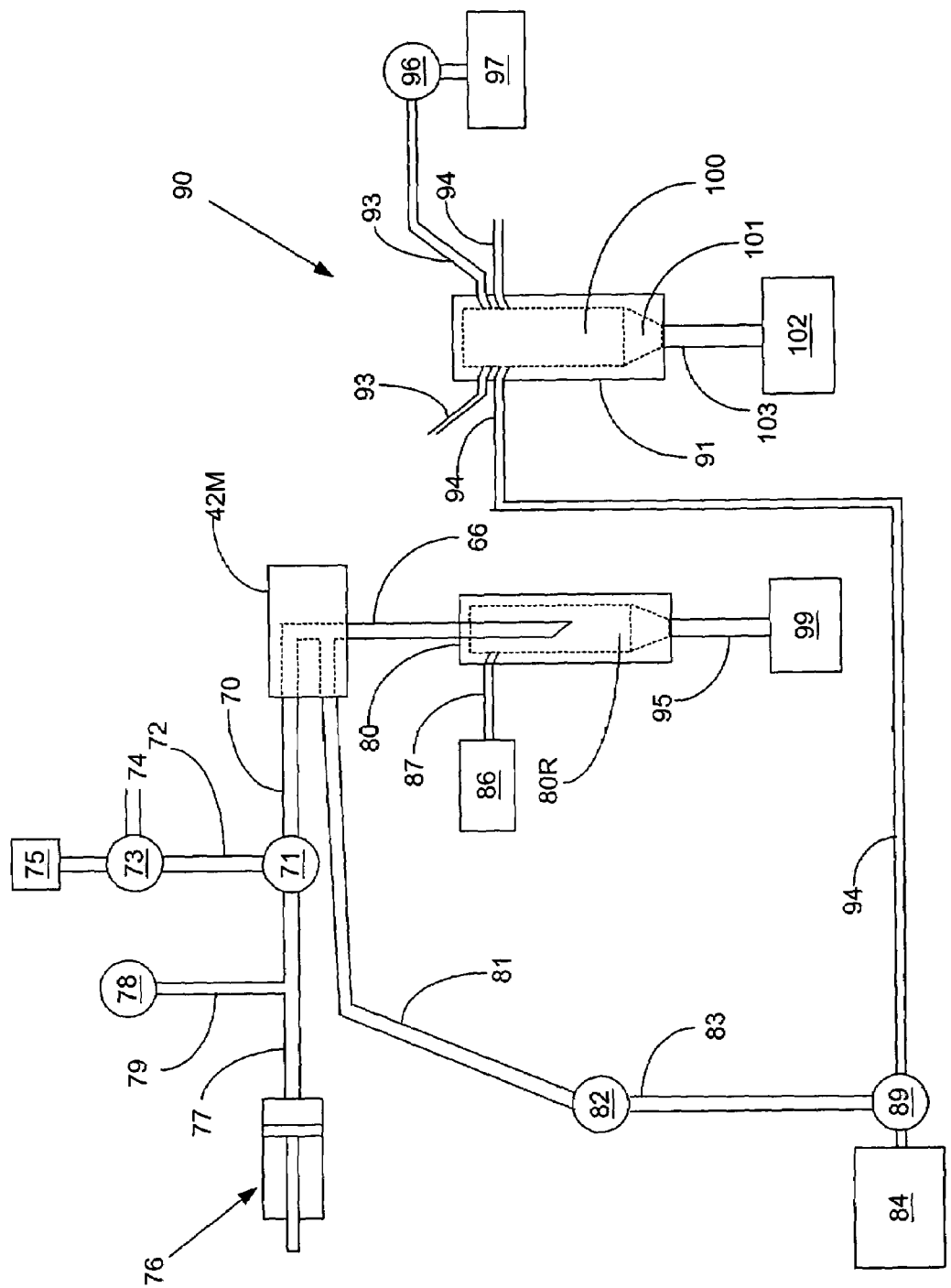
Figure 11B:
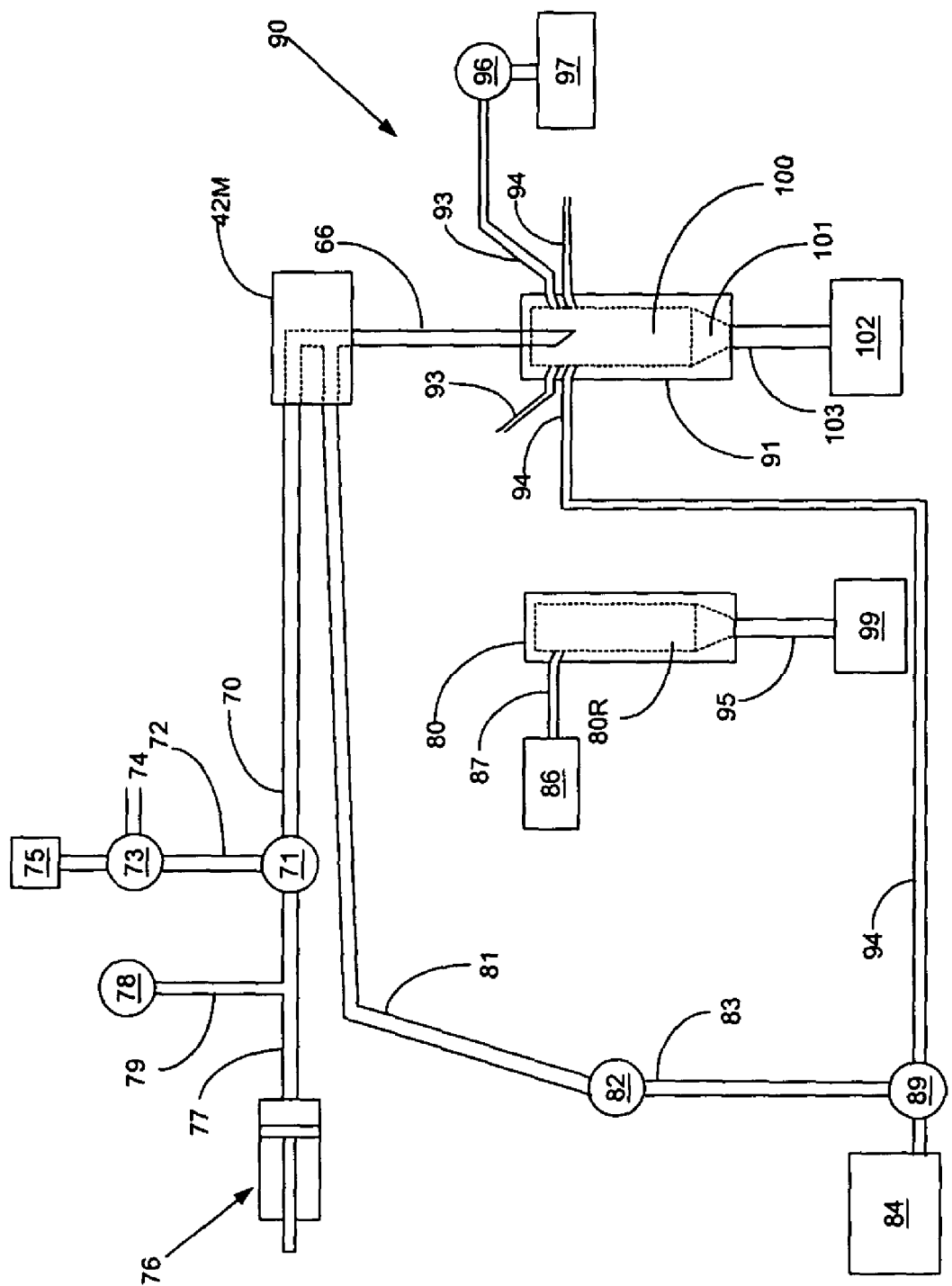
Figure 11C:
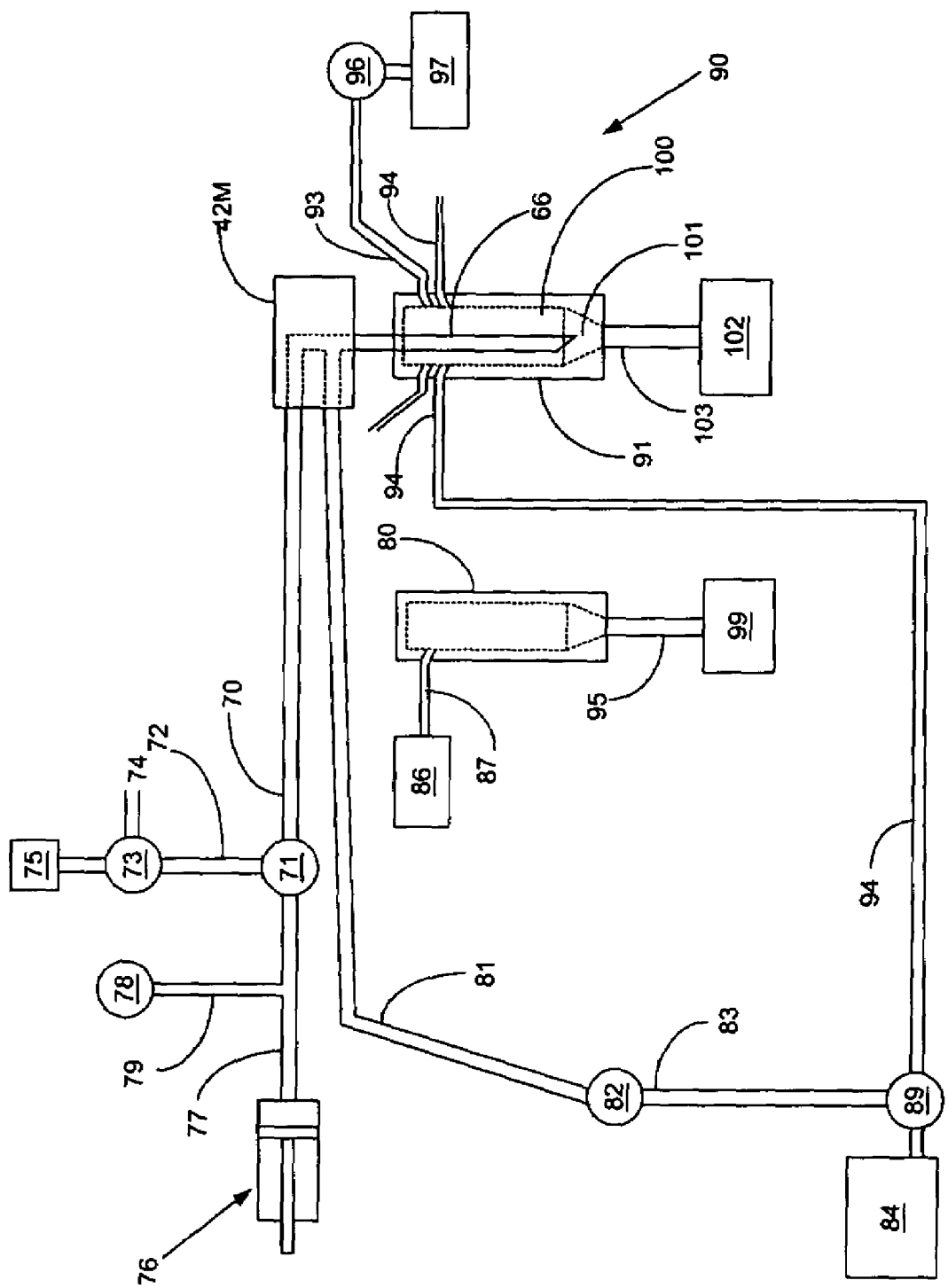

After probe 66 has dispensed sample fluid 68 into vessels 44V, it is advantageous to wash both the inside and outer surfaces of the probe 66 before its reuse on another sample fluid tube 40. FIGS. 11A–11C illustrate the present inventive method of cleansing sample fluid probe 66 so as to simultaneously achieve reduction of routine maintenance of a cleansing module 90 and sample fluid probe 66. As used herein, the term "cleansing" should be considered as potentially including aspirating cleansing solutions into the interior of probe 66, pumping rinsing liquid solutions through the interior of sample fluid probe 66, drying the interior of sample fluid probe 66 with air, and pumping rinsing liquid solutions against the exterior surface of sample fluid probe 66 and drying the exterior of sample fluid probe 66 with air. In particular a preferred method for using the cleansing module 90 includes inserting sample fluid probe 66 to full immersion within the internal reservoir 80R of second open cleansing body 80 and operating syringe pump 76 to aspirate a bleach-like cleansing solution from the internal reservoir 80R into probe 66, dispensing the cleansing solution back into internal reservoir 80R, removing probe 66 from the second open cleansing body 80 and inserting the probe 66 into the cleansing chamber 100 of the first cleansing body 91 while cleaning the exterior of probe 66, cleaning and rinsing and drying the interior of probe 66 while probe 66 is stationary within cleansing body 91, and finally rinsing and drying the exterior of probe 66 as it is withdrawn from cleansing body 91.

Figure 12:
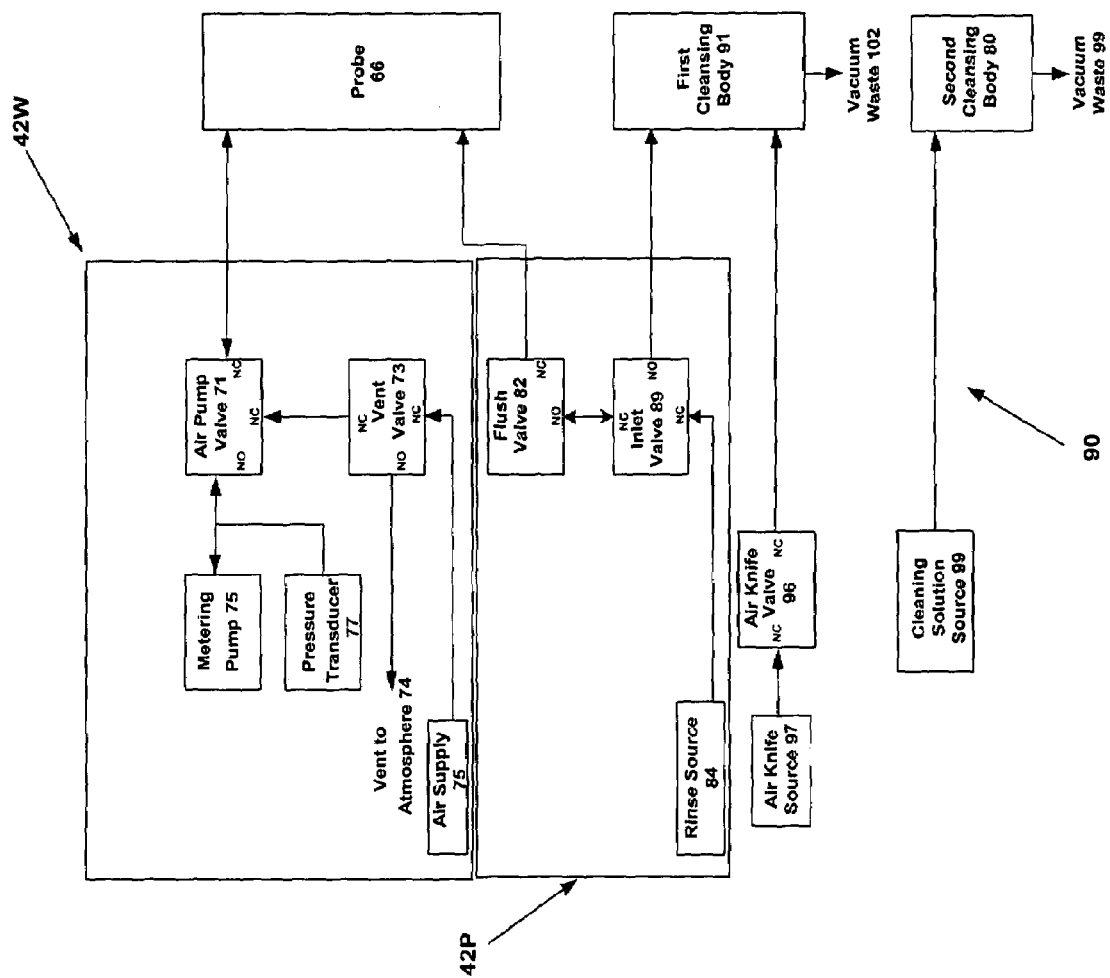
FIG. 12 is a fluidics diagram for the sampling system of the present invention.

The operation of the cleansing module 90 may be understood by reference to FIGS. 11A–11C and the fluidics diagram illustrated in FIG. 12. In a typical instance, illustrated in FIG. 11A, sample fluid probe 66 is axially positioned in alignment with the center of the second cleansing body 80, lowered into the internal reservoir 80R and syringe pump 76 is operated to aspirate a bleach-like cleansing solution from the internal reservoir 80R into probe 66 and maintain cleansing solution momentarily so that both the interior and exterior portions of probe 66 are brought into contact with the cleansing solution. Pump 76 is then operated to dispense the cleansing solution back into internal reservoir 80R. Alternately, pump 76 may be operated to maintain the cleansing solution within probe 66 until probe 66 next enters the first cleansing body 91 where it is expelled during a rinse of the interior of probe 66. This alternate cleansing step has the advantage of maintaining cleansing solution in contact with the interior of probe 66 for a longer period of time without increasing the time required for cleansing probe 66.

Sample fluid probe 66 is then axially positioned in alignment with the center of the first cleansing body 91, lowered into cleansing chamber 100 from the top of cleansing body 91, FIG. 11B, into the cleansing chamber 100 simultaneous with the onset of operating inlet valve 89 and pressurized rinse water source 84, thereby causing a rinsing flow of water to impinge upon the exterior of probe 66 as probe 66 is continued to be lowered into cleansing chamber 100 until the effective operating length of probe 66 is contained within cleansing chamber 100, as seen in FIG. 11C, where the downward motion of probe 66 is stopped. The cleaning solution and rinse water mixture is removed from cleansing chamber 100 through vacuum tube 103 by vacuum into waste reservoir 102. Preferable cleaning solutions include detergent water, Clorox™, alcohol, and sodium hydroxide and are pumped into the cleansing chamber 100 at a flow rate in the range of 1 to 2 ml/sec.

During a period of stationary action like depicted in FIG. 11C, the interior of probe 66 is cleansed as follows. Inlet valve 89 and flush valve 82 are activated so that a flushing water solution is caused to flow from pressurized rinse water source 84 through tubings 83 and 81 through the hollow portion of the sample fluid probe 66 within the cleansing chamber 100, thereby water rinsing the interior of the sample fluid probe 66. During this water rinsing process, valve 71 remains activated so that pressurized air is caused to flow from air source 75 through tubings 72 and 70 into manifold 42M and into the hollow portion of the sample fluid probe 66 along with the flow of rinsing water from pressurized rinse water source 84. Rinsing solution is removed from chamber 102 through vacuum tube 103 by vacuum into waste reservoir 102. A preferable rinsing water solution includes deionized water and is pumped through the sample fluid probe 66 into cleansing chamber 100 at a flow rate in the range of 1 to 2 ml/sec. An important feature of the present invention is the discovery of this pressurized rinsing solution flow as being superior in removing cleansing solution from the hollow interior surface of the sample fluid probe 66.

As a final step, valve 80 is deactivated so that no solutions pass through tubing 81; however, valve 71 is still activated so that pressurized air is caused to flow from air source 75 into manifold 42M and into the hollow portion of the sample fluid probe 66 drying the internal surface of probe 66. This final flow of drying air is an important improvement over probe cleaning systems in the prior art and is critical in effectively cleaning the interior portion of probe 66. It has been discovered that a flow of air in the range 3 to 10 liters/min is sufficient to create the drying air flow of the present invention that is effective in removing sample fluids from the interior of the sample fluid probe 66. As used herein, the term "effectively cleaning" should be considered as eliminating all but less than about 0.3 microliters of liquid from the interior surface of the sample fluid probe 66.

Subsequent to the process step of cleansing and drying the interior hollow portion of probe 66, probe 66 is removed from cleansing chamber 100 during which removal process, the exterior portion of probe 66 is dried until probe 66 has fully exited chamber 102, like seen in FIG. 10. The uppermost flow of pressurized air through tubing 93 is continued as probe 66 is extracted from chamber 102 so that an exterior drying flow of air also acts as an air knife in preventing any residue from clinging to probe 66 prior to its reuse in aspirating sample fluid from another sample fluid tube 40.

The combined operations of Pump Module 42P, Wash Module 42W and Cleansing Module 90 are operative to effect a first surprising result of thoroughly reducing carry-over of the washing liquids whereby the accuracy of sample fluid volume sensitive assays is increased. If an analyzer 10 is equipped with the wash resource of the present invention, it has been discovered that the cleaning air flow around the withdrawn sample fluid probe 66 is effective in removing most superfluous washing solutions to the extent that less than 0.03 microliters of liquid remains on exterior surface of the sample fluid probe 66. When the present invention is employed as described herein, variations in sample fluid volume sensitive assays, most notably for calcium, magnesium and glucose, are reduced in the range 10–50% in the instance that sample fluid volumes in the range 2 to 5 microliters are required in the assay.

The operations of Pump Module 42P, Wash Module 42W and Cleansing Module 90 are operative to effect a second surprising result of reducing the frequency of maintenance cleaning. If an analyzer 10 is equipped with the wash resource 42W of the present invention, it has been discovered that even more than 100,000 sample fluid aspirations can occur before the necessity for maintenance cleaning. Prior to the use of the particular wash resource 42W, maintenance cleaning was routinely scheduled in commercial installations after 3,000 sample fluid aspirations. While the mechanism for this improved performance is not fully understood, it can be supposed that the feature of full immersion of the sample fluid probe 66 within the cleansing chamber 100 during washing of the sample fluid probe 66 is a contributing factor.

Figure 13:
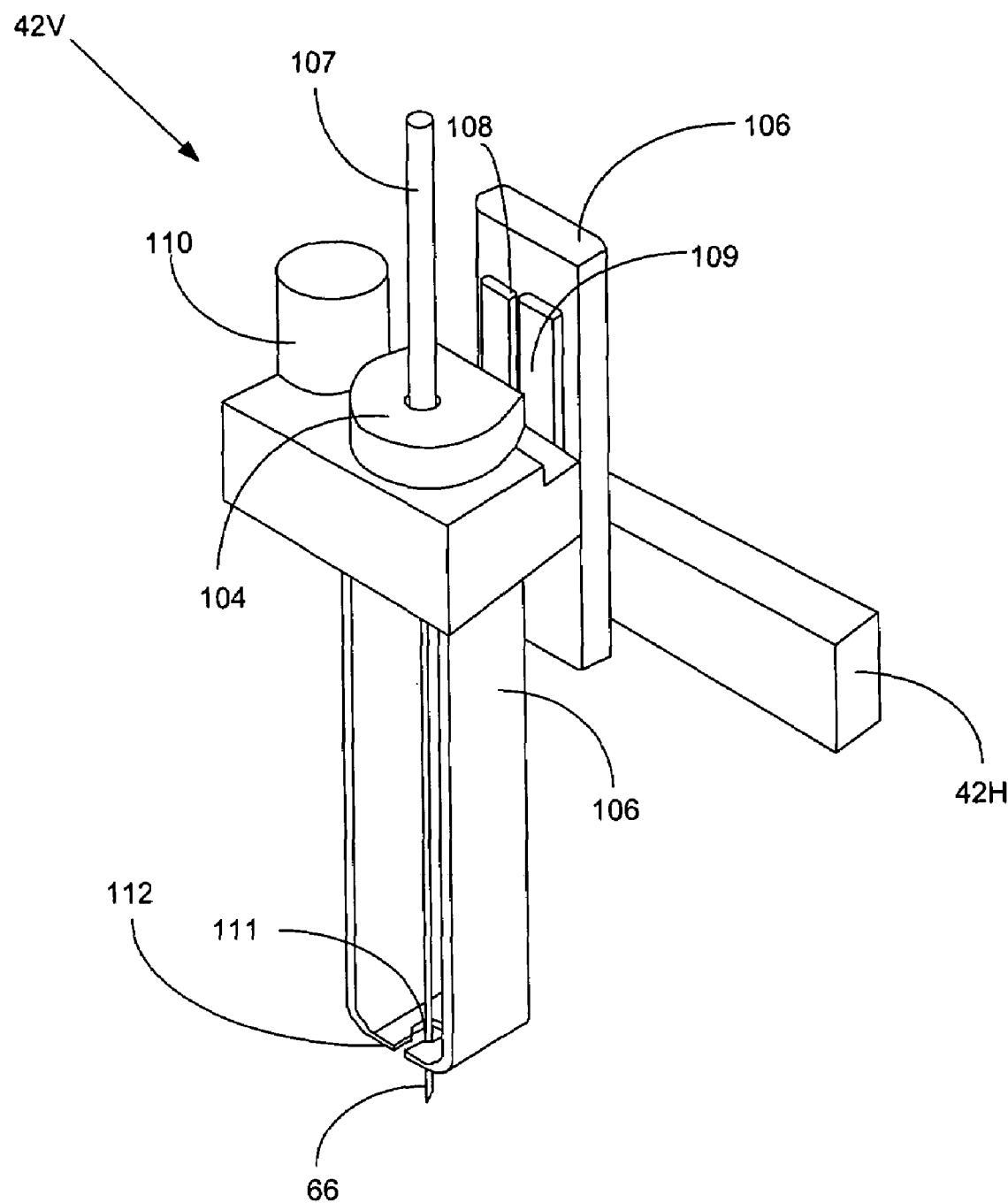
FIG. 13, 14, 14A, 14B describe a sampling aliquotter exemplifying the present invention; and, FIGS. 15A–15H describe the operation of the sampling aliquotter of FIG. 13.

An important feature of the present invention is the cost-effective use of manifold 42M as a portion of wash resource 42W as well as its use in a through-the-closure tube aspirating and puncturing Vertical Drive 42V, illustrated in FIG. 13. Vertical Drive 42V comprises a linear actuator 104 with a free drive screw adapted to vertically drive probe 66 through an opening 111 in a flat bottom portion 112 of a sample fluid tube retainer 106. The linear actuator 104 is preferably a stepping motor with a hard plastic nut in place of the actuator's central rotor shaft. A leadscrew 107 passes through the nut and attaches to probe 66 (which provides the anti-rotation feature for the screw). As the motor rotor turns, the leadscrew 107 moves vertically through the linear actuator 104.

Two linear slides guide the vertical motions of Vertical Drive 42V. The first linear slide 108 has two carriages and allows the sample fluid tube retainer 106 to travel vertically relative to the horizontal drive 42H. The two carriages provide additional stability to the Vertical Drive 42V. The second linear slide 109 allows probe 66 to travel vertically relative to the tube retainer 106. The Vertical Drive 42V has at least two position sensors, and a capacitive sensor for sample fluid level detection. One sensor is a "Probe Home" sensor, and detects when probe 66 is fully retracted into tube retainer 106. A second sensor is the "tube retainer position" sensor, which detects if tube retainer 106 is in its full up (retracted) position. A third sensor is a liquid level detection sensor, which utilizes capacitance measurements to sense when probe 66 contacts a conductive object, thereby changing its capacitance. The Horizontal Drive 42H typically consists of a conventional motorized linear slide as illustrated in FIG. 13 and is adapted to position the Vertical Drive 42V over one of sample fluid tubes 40 on a rack 38, individual vessels 44V of aliquot vessel arrays 44, and Cleansing Module 90 as indicated by dashed lines and illustrated in FIG. 7.

Figure 14:
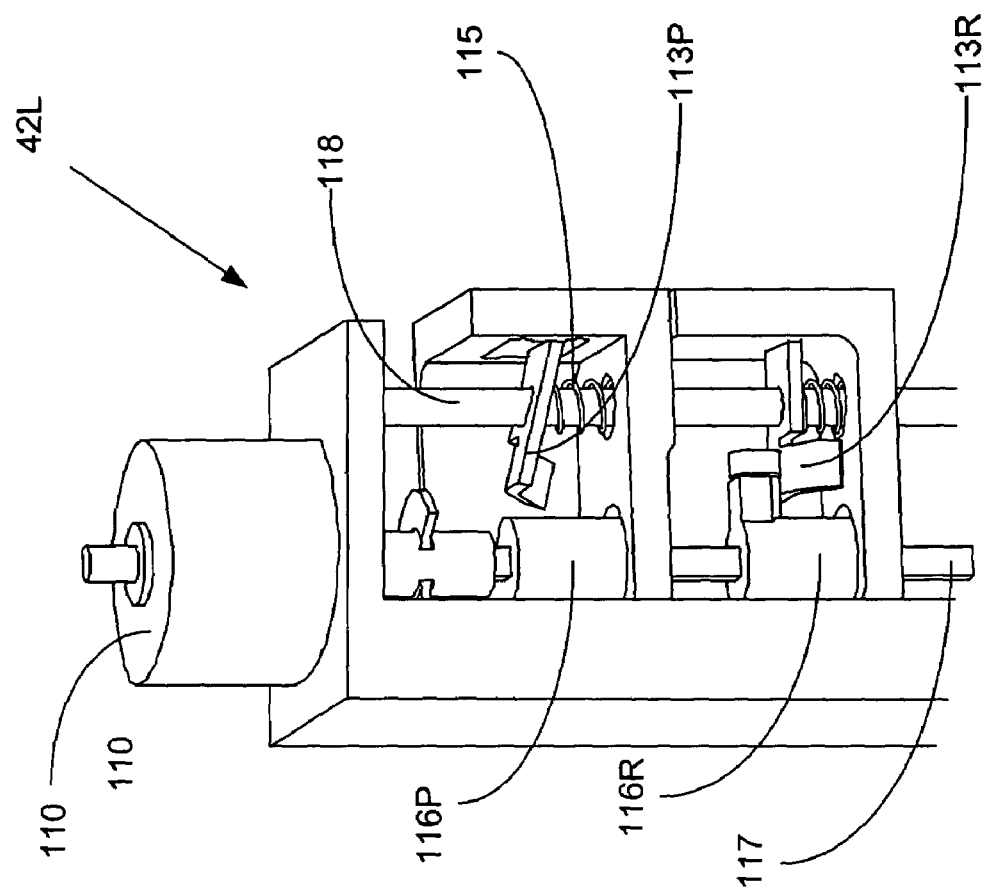

A Rotary Pneumatic Actuator 110 provides the motive force for a lock mechanism illustrated in FIG. 14. A solenoid valve directs air pressure to one side of actuator 110, while venting the opposite side to atmosphere. This causes actuator 110 to rotate 90 degrees. When power is removed from the solenoid valve, air pressure is supplied to the side previously vented, causing actuator 110 to rotate back. Thus, unlike a typical electrical rotary solenoid, both directions of travel are under power as opposed to a spring return. This coupled with the mechanical advantage of pneumatic energy, provides for a high level of controlled torque.

Sample fluid tube retainer 106 supports the vertical drive motor while also providing features for retaining tubes 40 in the tube rack 38 as probe 66 is retracted from a closure 69. The lower portion 112 of tube retainer 106 is designed to sit atop sample fluid tubes 40 with a bore 111 through the lower portion 112 through which probe 66 travels. Bore 111 is of a large enough diameter to allow the "nose" of a "Sarstedt™" sample fluid tube 40 to fit within it so that tube retainer 106 sits on the outer rim of such a sample fluid tube 40. Other sample tubes 40 generally have a flat top-closure 69 larger than bore 111 so that the Vertical Drive 42V is suitable for use with a wide variety of sample tubes 40.

Figure 14A:
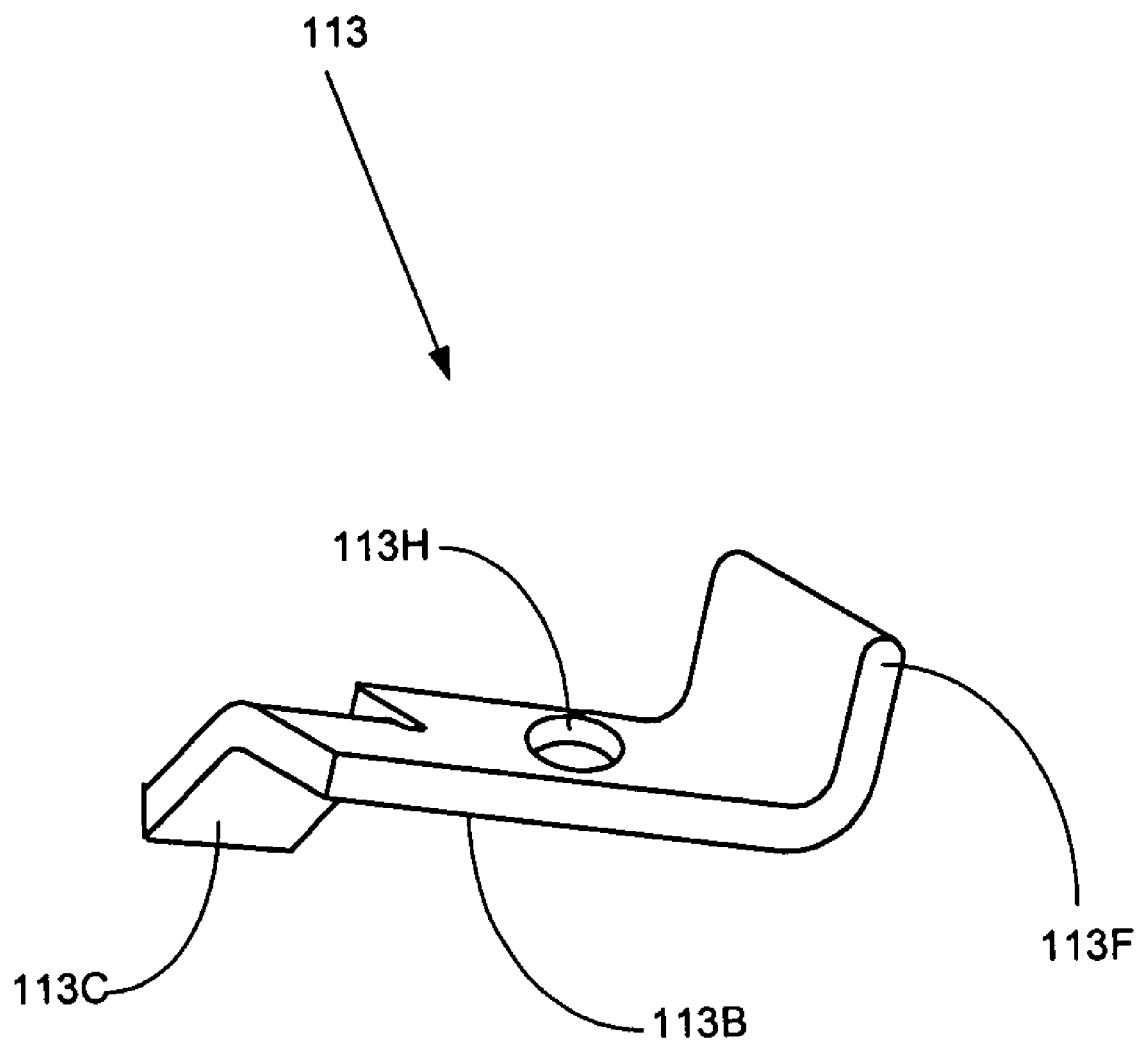
Figure 14B:
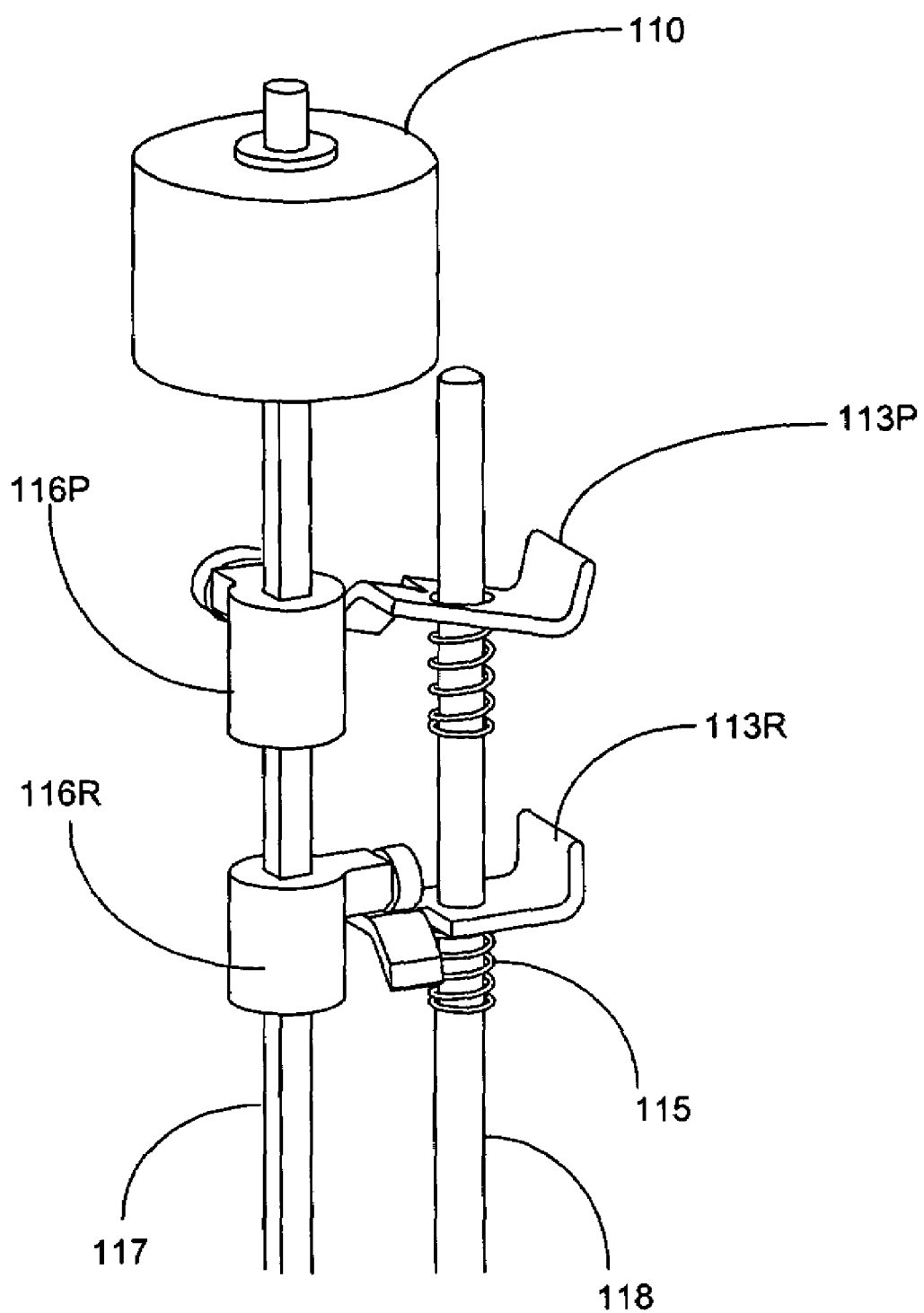

A Locking Mechanism 42L seen in FIG. 14 alternately locks probe 66 or tube retainer 106 in the vertical direction, allowing the single linear actuator 110 to perform two functions. The mechanism uses the principle of frictional binding to provide a locking force. An L-shaped binding clip 113 having the short, foot portion 113F of the L generally perpendicular to the back portion 113B of the L-shaped binding clip 113, has a hole 113H in the back portion 113B through which a stationary shaft 118 passes. A top portion of the back portion 113B is partially cut and bent in the direction opposite from the foot portion 113F in order to form a cam surface 113C. FIG. 14A is an enlarged view of binding clip 113 illustrating these features. The foot portion 113F of the L-shaped binding clip 113 rests on the component to be locked, only one of either probe 66 or tube retainer 106. A spring 115 forces the binding clip 113 upward, rotating it so that the foot portion 113F of the L is brought into binding contact with the component to be locked. This rotation causes the hole 113H in the clip 113 to bind against the stationary shaft 114. As long as the moment arm between the hole 113H and the back portion 113B is sufficiently larger than the diameter of the hole, for example 2:1, the friction generated will always be greater than the force applied to move the locked component (i.e., the more force applied to move the component, the harder the binding clip 113 grips). This mechanism uses the same principle as do the binding clips used on some caulking guns.

To unlock clip 113P, a cam 116P is rotated against clip 113P on the side opposite of the "L". The cam forces clip 113P to a level position, unbinding clip 113P and the shaft, and providing freedom of movement to the locked component. The cam 116P is a ball bearing attached to a collar with a square hole through it. A square shaft 117 passes through this hole. The square shaft 117 is attached to the rotary actuator 110. Thus cam 116P may be rotated into and out of position. The cam 116P is mounted to the locked component by a radial ball bearing, and rides vertically with the component.

Both probe 66 and tube retainer 106 have a binding clips 113P and 113R riding on a common round shaft 118. The cams 116P and 116R for the two mechanisms are rotated 90 degrees from each other, so that when either probe 66 or tube retainer 106 is engaged (unlocking that particular binding clip 113), the other is disengaged (allowing its binding clip 113 to lock). Rotating the square shaft 117 unlocks one binding clip 113 while locking the other binding clip 113. (When the lock is de-energized, probe 66 is unlocked and tube retainer 106 is locked). At the center of travel, both clips are in the lock position so that both components cannot be unlocked at the same time, which would result in the entire vertical drive 42V falling, as the binding clips 113 support the entire moving mechanism.

FIG. 14A is an enlarged view of the components of locking mechanism 42L and better shows how one cam 116P and binding clip 113P while locking the other cam 113R and binding clip 113R are associated with controlling the vertical locking of probe 66 and tube retainer 106, respectively, as described later.

A unique characteristic of the locking mechanism 42L is that when locked, the locked component, either probe 66 or tube retainer 106, is prevented from moving downwards, but is completely free to move upwards. This attribute is taken advantage of when withdrawing the probe 66 from the tube closure 69. When probe 66 is in the a sample fluid tube 40, the lock mechanism 42L is activated, unlocking the tube retainer 106 and locking the probe 66. The tube retainer 106 is moved downwards until it contacts a tube 40. Once the tube 40 stops motion of the tube retainer, probe 66 automatically begins to move upwards. (Linear actuator 110 is closing the distance between actuator 110 and the probe 66; it's irrelevant which component is actually moving). Thus a single continuous motion is used to lower the retainer 106 and retract the probe 66.

An alternate embodiment of the locking mechanism 42L employs a single shaft instead of separate round shafts 118 and square shafts 117. In this configuration, the square cam shaft 117 serves both as the rotating element and the binding shaft. The binding clip 113 would have a square hole through it, and be attached to a collar on the square shaft 117. This collar is connected to the component to be locked (either probe mount or tube retainer). The "cam" would now be stationary. When the square shaft 117 is rotated by actuator 110, both the collar and the binding clip 113 rotate with it. Thus, to disengage the lock, the binding clip 113 is rotated into the stationary cam instead of the cam rotating into the binding clip. This configuration reduces the size of the locking mechanism 42L, and allows the locking mechanism 42L to be a separate subassembly that is attached to the probe 66 and tube retainer 106, rather than an integral part of the overall Vertical Drive 42V.

FIGS. 15A–G illustrate schematically the operation of locking mechanism 42L in providing the movements needed to puncture a tube closure 69 and aspirate a desired amount of sample fluid with probe 66, finally removing probe 66 from the closure 69. In these figures, the binding clip 113 for probe 66 and tube retainer 106 are separately identified as 113P and 113R, respectively.

Figure 15B:
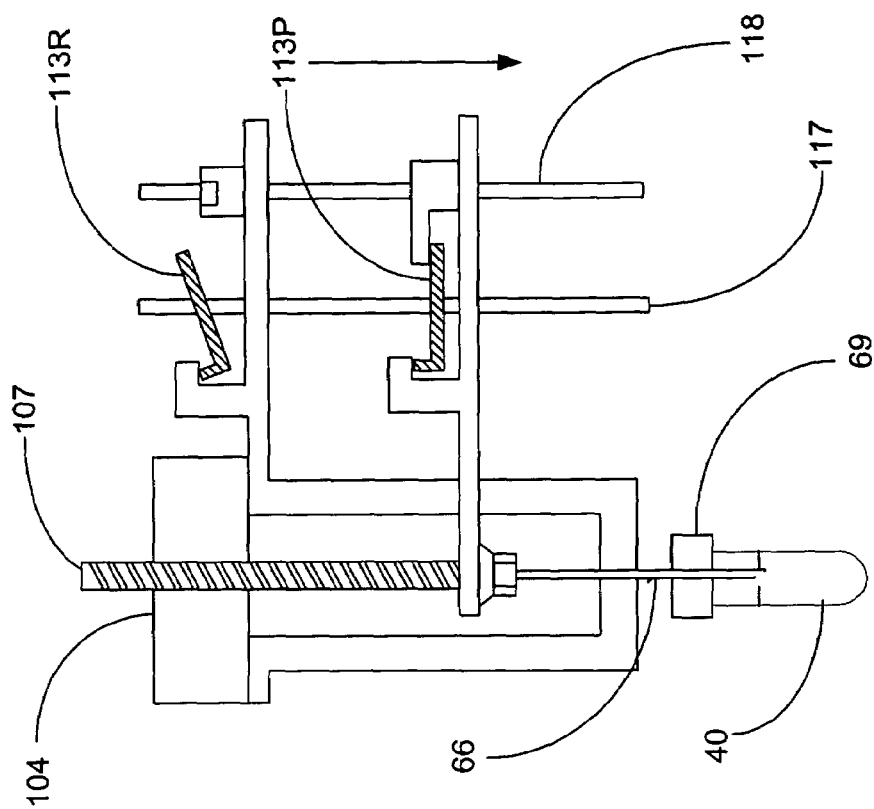
Figure 15A:
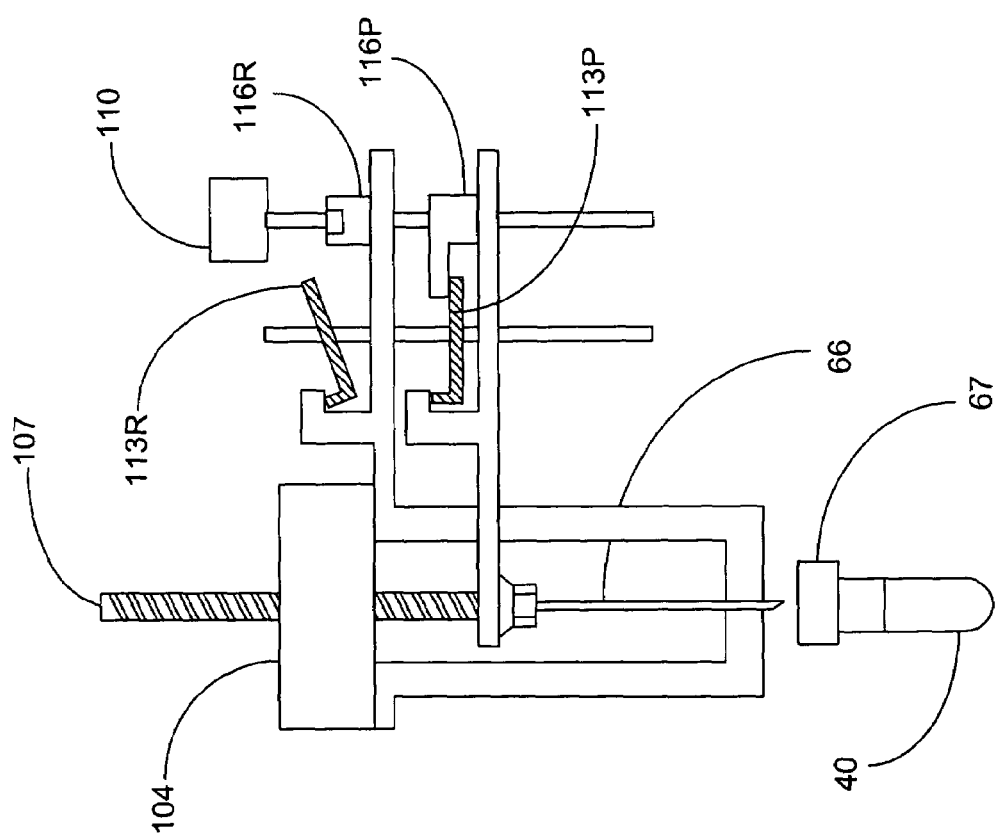

FIG. 15A: Rotary actuator 110 is operated to move cam 116R so that probe lock 113P is in its "unlocked" state, providing probe 66 with freedom of vertical movement, but "locking" probe retainer clip 113R. The weight of the Vertical Drive 42V is supported by the tube retainer clip 113R.

FIG. 15B: Linear actuator 104 runs in a first direction that moves leadscrew 107 (and probe 66) downward, increasing the distance between the actuator 110 and probe 66 and puncturing closure 69. An arrow is positioned proximate probe lock 113P to indicate its "downward" movement.

Figure 15D:
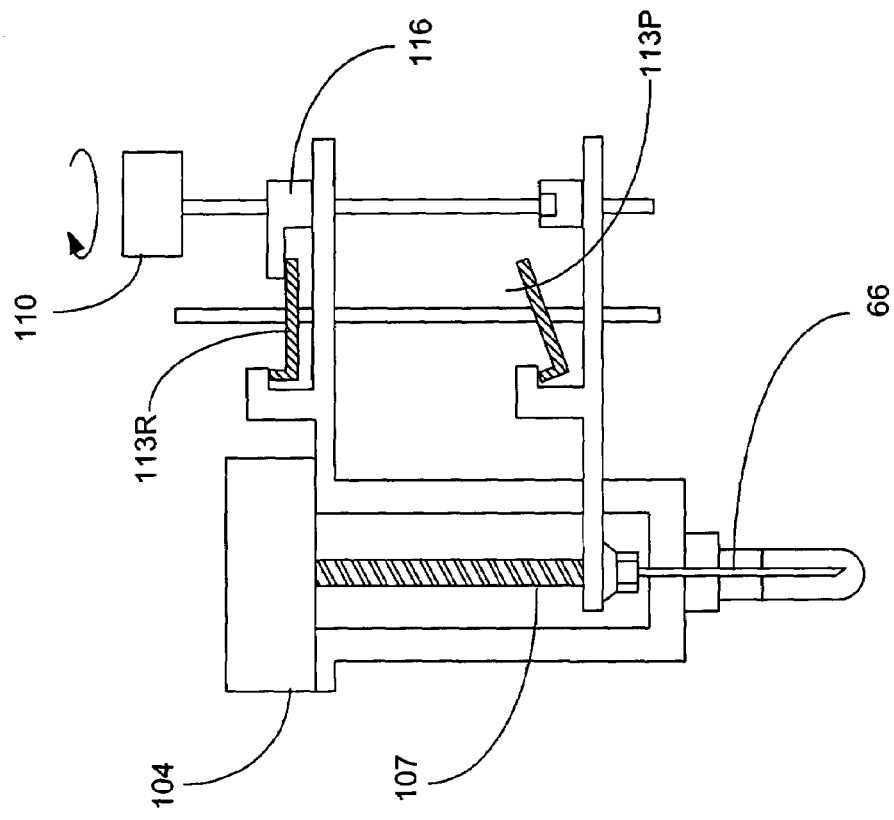
Figure 15C:
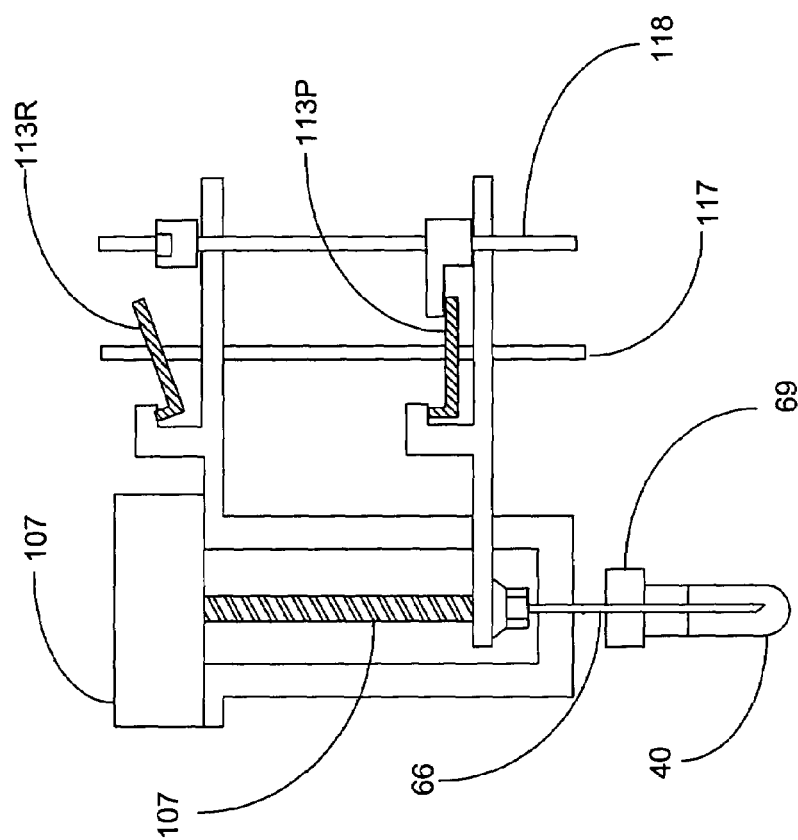

FIG. 15C: Probe 66 reaches the limit of its downward movement, tube 40 is vented, sample fluid level is detected, and the desired amount of sample fluid is aspirated.

FIG. 15D: Rotary actuator 110 is operated to rotate cam 116P so as to activate probe lock 113P, thereby locking probe 66 and unlocking tube retainer 106. The weight of the Vertical Drive 42V is now applied to the probe lock 113P.

Figure 15F:
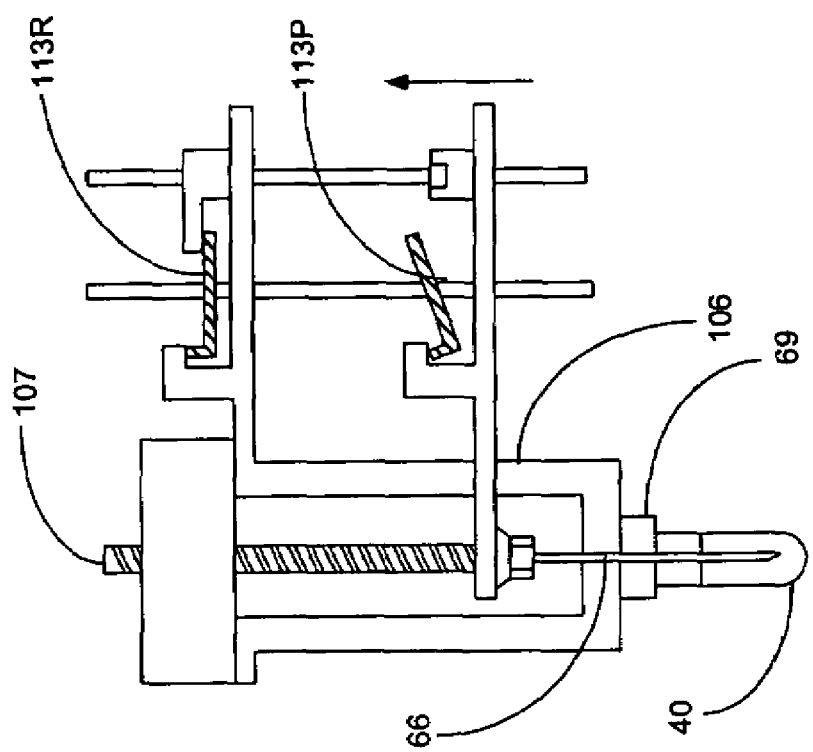
Figure 15E:
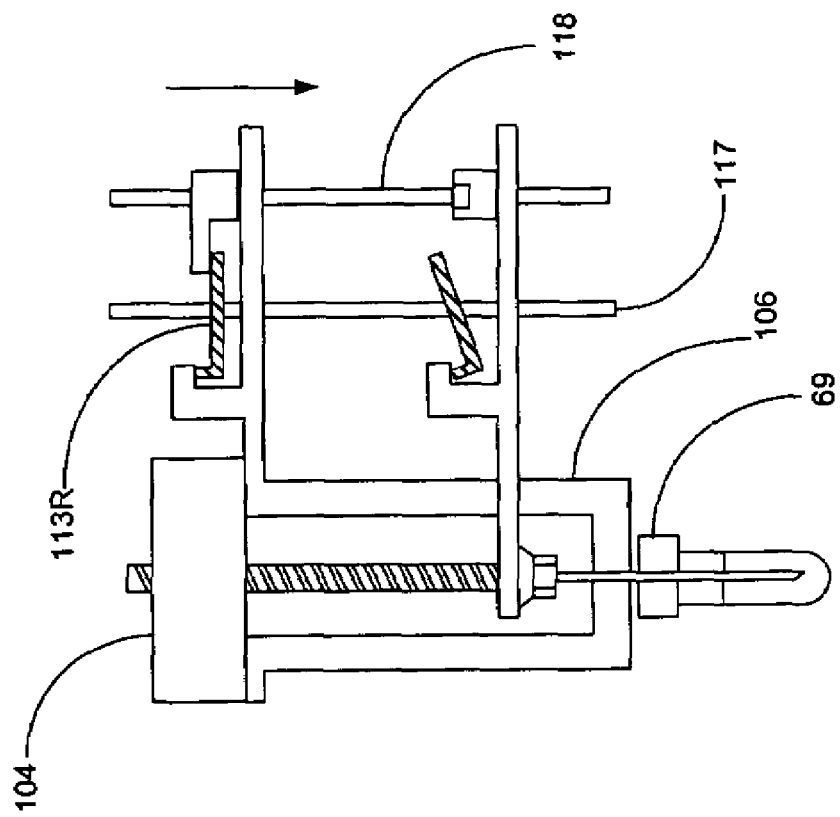

FIG. 15E: Linear actuator 104 runs in a second direction opposite to the first direction so that the distance between probe 66 and actuator motor 104 is reduced. Since the weight of the Vertical Drive 42V is supported by the probe lock 113P, and the tube retainer 106 is free to move vertically, tube retainer 106 moves downward as indicated by the arrow proximate lock 113R (essentially, the linear actuator 110 moves along a stationary leadscrew 107).

FIG. 15F: Once tube retainer 106 contacts the top of tube 40, its downward motion is halted. However, although probe 66 is locked from moving downward, probe lock 113P does not prevent probe 66 from moving upward. Therefore, the action of linear actuator 110 causes probe 66 to immediately begin to move upward, indicated by the arrow proximate lock 113P, retracting from closure 69 and tube 40. The number of leadscrew 107 turns to move tube retainer 106 down and retract probe 66 is identical to the number originally required to move probe 66 downward to the sample fluid. A key feature of this design is that the tube 40 is only restrained by tube retainer 106 with an amount of force required to extract the probe from closure 69 so that a separately activated tube restrainer is not needed. Furthermore, such a separately activated restrainer would have to restrain all tubes with a same maximum force, unnecessarily endangering smaller tubes.

Figure 15H:
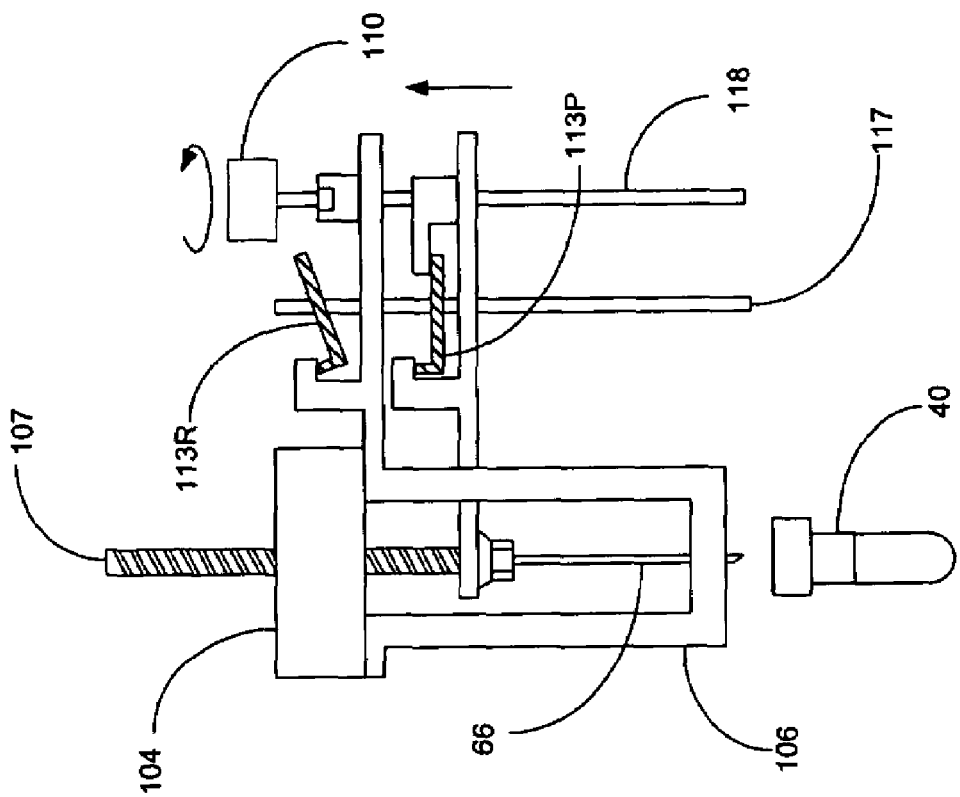
Figure 15G:
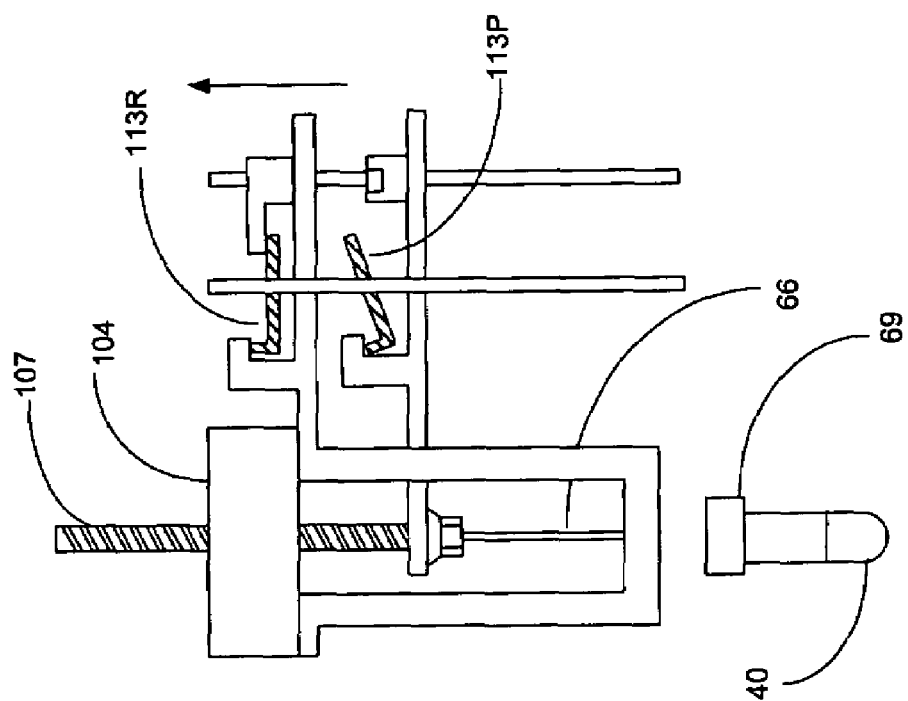

FIG. 15G: Once probe 66 is out of the tube 40 and in its "home" position relative to the retainer 106, the linear actuator 110 is run in the first direction, causing tube retainer 106 to rise, indicated by the arrow proximate lock 113R (increasing the distance between the actuator motor 110 and probe 66). Probe 66 is still locked from moving downward. The tube retainer 106 moves upward until it is fully retracted.

FIG. 15H: Rotary actuator 110 is rotated so that probe lock 113P is deactivated, retainer lock 113R is activated, thereby restraining the tube retainer 106 and freeing probe 66. The linear actuator 104 is again activated in the reverse direction (reducing the distance between the actuator 104 and probe 66), causing probe 66 to retract, indicated by the arrow proximate lock 113P. The number of leadscrew 107 turns for probe 66 to reach its home position is the same as the number required by the tube retainer 106 to fully retract (in step 7).

In step 3 above, after sample fluid level has been determined, sample fluid aspiration commences as follows. A vacuum generated by piston-type syringe pump 76 (FIG. 8) draws sample fluid 68 up into the probe. At the same time, probe 66 descends to follow the level of the sample down in the tube 40, keeping the tip immersed in sample fluid 68. After aspiration is completed, a pressure profile recorded during the event is examined, and probe 66 is retracted from sample tube 40. Finally, a quantity of air is aspirated into probe 66 by pump 66 to move sample fluid 68 away from the probe bottom to prevent potential drips. The rate of aspiration (speed of pump 76) is chosen to provide a pressure profile with the features like those disclosed in U.S. Pat. No. 6,370,942 necessary for a aspiration free of errors while minimizing cycle time.

Preferably, probe 66 is fabricated from series 316, stainless steel, eighteen gauge, heavy wall, smooth bore tubing and has a free length on the order of four-six inches. The lower end of probe 66 has a deflected point (visible in FIG. 9) that eliminates coring when probe 66 passes through closure 69. Although a probe 66 having such dimensions as set forth above might be expected to buckle upon penetration of elastomeric materials, vertical drive 42V utilizes colinear forces between closure 69, actuator 104 and probe 66 thereby preventing such an occurrence.

The use of manifold 42M in cleaning the interior and exterior portions of probe 66, in combination with the use of manifold 42M during aspiration of sample fluid from closed sample tube 40 by lowering manifold 42M inside tube retainer 106 is an important conservation and multiple use of the liquid sampling aliquotter 42 of the present invention. Those skilled in the art, having the benefit of the teachings of the present invention as hereinabove set forth may effect numerous modifications thereto. It should be understood that these- and other modifications lie within the scope of the present invention as set forth in the appended claims.

What is claimed is:

1. A sampling aliquotter system for aspirating with a probe aliquot portions of sample fluid from a sample fluid tube closed by a closure and for dispensing said aliquot portions into a vessel, said aliquotter comprising:
 a sample fluid tube closed by a closure;
 a horizontal drive, a vertical drive, a probe depending from said vertical drive, a pump module and a cleansing module, the horizontal drive adapted to position the vertical drive above the sample fluid tube, the vessel and the cleansing module,
 wherein the vertical drive comprises a linear actuator configured to drive the probe through the closure,
 wherein the pump module being configured to aspirate and dispense sample fluid through the probe,
 the cleansing module being configured to cleanse the sample fluid probe,
 and wherein the vertical drive further comprises a retainer with a first and second clips mounted on a single round shaft, the clips rotatable between a binding position and a free position by a single rotary actuator and configured such that either: (a) the first dip binds the probe and the second dip releases the retainer, or (b) the second dip binds the retainer and the first dip binds the probe.

2. The sampling aliquotter of claim 1 wherein the vertical drive comprises a linear actuator and a sample tube retainer, the linear actuator operable to drive the probe through the closure, lower the tube retainer into contact with the closure, retract the probe from the closure and raise the tube retainer off the closure.

3. The sampling aliquotter of claim 1 wherein the cleansing module comprises a cleansing body having a cleansing chamber formed therein to receive the probe, the cleansing body having two pairs of tubings ported thereto, a first pair of tubing connected to an air knife supply source, a second pair of tubing connected to a pressurized rinse water source, the air knife source activated when the probe is lowered by the vertical drive into the cleansing chamber, the pressurized rinse water source activated when the probe is removed from the cleansing chamber by the vertical drive.

4. The sampling aliquotter of claim 1 further comprising a wash module adapted to pump a cleaning solution through the probe along with a flow of pressurized air from the pump module.

5. The sampling aliquotter of claim 1 wherein the cleansing chamber is in vacuum communication with a waste reservoir.

* * * * *

UNITED STATES PATENT AND TRADEMARK OFFICE
CERTIFICATE OF CORRECTION

PATENT NO. : 7,186,378 B2
APPLICATION NO. : 10/623354
DATED : March 6, 2007
INVENTOR(S) : William D. Dunfee It is certified that error appears in the above-identified patent and that said Letters Patent is hereby corrected as shown below:

1) In Claim 1, column 16, line 61, please delete the word "dip" and insert -- clip --.
2. In Claim 1, column 16, line 62, please delete the word "dip" and insert -- clip --.
3. In Claim 1, column 16, line 63, please delete the word "dip" after "second", and before "binds" and insert -- clip --.
4. In Claim 1, column 16, line 63, please delete the word "dip" after "first", and before "binds" and insert -- clip --.

Signed and Sealed this

Eighteenth Day of March, 2008

JON W. DUDAS
*Director of the United States Patent and Trademark Office*